(12) United States Patent
Michaelsen et al.

(10) Patent No.: US 9,891,234 B2
(45) Date of Patent: Feb. 13, 2018

(54) BIOCHEMICAL MARKERS FOR CVD RISK ASSESSMENT

(75) Inventors: Natasha Barascuk Michaelsen, Kobenhavn S (DK); Federica Genovese, Kobenhavn O (DK); Morten Karsdal, Kobenhavn O (DK); Diana Julie Leeming, Espergaerde (DK)

(73) Assignee: Nordic Biociences A/S, Herlev (DK)

( * ) Notice: Subject to any disclaimer, the term of this patent is extended or adjusted under 35 U.S.C. 154(b) by 1031 days.

(21) Appl. No.: 14/116,924

(22) PCT Filed: May 4, 2012

(86) PCT No.: PCT/EP2012/058289
§ 371 (c)(1),
(2), (4) Date: Nov. 19, 2014

(87) PCT Pub. No.: WO2012/152716
PCT Pub. Date: Nov. 15, 2012

(65) Prior Publication Data
US 2015/0118698 A1    Apr. 30, 2015

(30) Foreign Application Priority Data
May 12, 2011   (GB) .................................. 1107922.5

(51) Int. Cl.
| | |
|---|---|
| *G01N 33/53* | (2006.01) |
| *G01N 31/00* | (2006.01) |
| *G01N 33/68* | (2006.01) |
| *C07K 16/18* | (2006.01) |
| *C12Q 1/37* | (2006.01) |
| *C07K 14/47* | (2006.01) |

(52) U.S. Cl.
CPC ..... *G01N 33/6893* (2013.01); *C07K 14/4725* (2013.01); *C07K 16/18* (2013.01); *C12Q 1/37* (2013.01); *G01N 33/6878* (2013.01); *C07K 2317/34* (2013.01); *G01N 2800/32* (2013.01); *G01N 2800/323* (2013.01)

(58) Field of Classification Search
None
See application file for complete search history.

(56) References Cited

U.S. PATENT DOCUMENTS

| | | | | |
|---|---|---|---|---|
| 9,206,464 | B2 * | 12/2015 | Veidal ...................... | C12Q 1/37 |
| 9,359,633 | B2 * | 6/2016 | Karsdal ................ | C07K 14/775 |
| 9,404,932 | B2 * | 8/2016 | Veidal .................... | C07K 14/78 |
| 9,459,206 | B2 * | 10/2016 | Xu ..................... | G01N 21/4738 |
| 9,500,659 | B2 * | 11/2016 | Leeming ................ | C07K 16/18 |
| 9,606,130 | B2 * | 3/2017 | Veidal ................ | G01N 33/6893 |

FOREIGN PATENT DOCUMENTS

| | | |
|---|---|---|
| WO | 2009/059972 A2 | 5/2009 |
| WO | 2010/046443 A2 | 4/2010 |

OTHER PUBLICATIONS

Karsdal et al. (Clinical Biochemistry, vol. 43, No. 10-11, Jul. 1, 2010, pp. 793-804).*
Barascuk et al. (Clinical Biochemistry, vol. 44, No. 10-11, Apr. 30, 2011, pp. 900-906).*
Veidal et al., (Disease Markeres; 28, pp. 15-28, 2010).*
Tascilar et al. (Annals of Oncology 10,Suppl. 4:S107-S110, 1999).*
Tockman et al. (Cancer Research 52:2711s-2718s, 1992).*
Mayne, R. Collagenous proteins of blood vessels. Arteriosclerosis 1986; vol. 6: pp. 585-593; entire document.
McCullagh, KG et al. The distribution of collagen types I, III and V (AB) in normal and atherosclerotic human aorta. J. Pathol. 1980; vol. 130(1): pp. 45-55; entire document.
Mecham, RP et al. Elastin degradation by matrix metalloproteinases: cleavage site specificity and mechanisms of elastolysis. J. Biol. Chem. 1997; vol. 272(29): pp. 18071-18076; entire document.
Mendall, MA et al. C reactive protein and its relation to cardiovascular risk factors: a population based cross sectional study. BMJ 1996; vol. 312: pp. 1061-1065; entire document.
Monfort, J et al. Chondroitin sulfate and hyaluronic acid (500-730 kda) inhibit stromelysin-1 synthesis in human osteoarthritic chondrocytes. Drugs Exptl. Clin. Res. 2005; vol. 31(2): pp. 71-76; entire document.
Moreno, PR et al. Macrophage infiltration in acute coronary syndromes. Implications for plaque rupture. Circulation 1994; vol. 90: pp. 775-778; entire document.
Pasceri, V et al. Direct proinflammatory effect of C-reactive protein on human endothelial cells. Circulation 2000; vol. 102: pp. 2165-2168; entire document.
Register, TC et al. Effects of soy isoflavones and conjugated equine estrogens on inflammatory markers in atherosclerotic, ovariectomized monkeys. J. Clin. Endocrinol. Metab. 2005; vol. 90: pp. 1734-1740; entire document.
Reynolds, GD et al. C-reactive protein immunohistochemical localization in normal and atherosclerotic human aortas. Arch. Pathol. Lab. Med. 1987; vol. 111: pp. 265-269; entire document.
Ridker, PM. Intrinsic fibrinolytic capacity and systemic inflammation: novel risk factors for arterial thrombotic disease. Haemostasis 1997; vol. 27: pp. 2-11; entire document.
Ridker PM, et al. C-reactive protein and other markers of inflammation in the prediction of cardiovascular disease in women. New Engl. J. Med. 2000; vol. 342: pp. 836-843; entire document.
Rodriguez-Lee, M et al. Fatty acid-induced atherogenic changes in extracellular matrix proteoglycans. Curr. Opin. Lipidol. 2007; vol. 18: pp. 546-553; entire document.

(Continued)

*Primary Examiner* — Lisa V Cook
(74) *Attorney, Agent, or Firm* — Benjamin Aaron Adler

(57) ABSTRACT

A method of bioassay for the quantification of peptide fragments comprising a neo-epitope formed by cleavage of mimecan, a protein of an atherosclerotic plaque, by a proteinase is provided. In the method a sample, such as urine or serum, is contacted with an antibody reactive with the neo-epitope and the level of binding of the antibody to peptide fragments in the sample is determined. The assay is predictive of risk of cardiovascular disease events.

7 Claims, 4 Drawing Sheets

(56) References Cited

OTHER PUBLICATIONS

Rosenquist, C et al. Serum crosslaps one step ELISA. First application of monoclonal antibodies for measurement in serum of bone-related degradation products from C-terminal telopeptides of type I collagen. Clin. Chem. 1998; vol. 44(11): pp. 2281-2289.

Rouis, M. Matrix metalloproteinases: a potential therapeutic target in atherosclerosis. Curr. Drug Targets. Cardiovasc. Haematol. Disord. 2005; vol. 5: pp. 541-548; entire document.

Rudel, LL et al. Hepatic origin of cholesteryl oleate in coronary artery atherosclerosis in African green monkeys. Enrichment by dietary monounsaturated fat. J. Clin. Invest. 1997; vol. 100: pp. 74-83; entire document.

Salisbury, BGJ et al. Isolation and preliminary characterization of proteoglycans dissociatively extracted from human aorta. J. Biol. Chem. 1981; vol. 256(15): pp. 8050-8057; entire document.

Satta, J et al. Increased turnover of collagen in abdominal aortic aneurysms, demonstrated by measuring the concentration of the aminoterminal propeptide of type III procollagen in peripheral and aortal blood samples. J. Vasc. Surg. 1995; vol. 22: pp. 155-160; entire document.

Schaar, JA et al. Current diagnostic modalities for vulnerable plaque detection. Curr. Pharm. Des. 2007; vol. 13: pp. 995-1001; entire document.

Shanahan, CM et al. Identification of osteoglycin as a component of the vascular matrix. Differential expression by vascular smooth muscle cells during neointima formation and in atherosclerotic plaques. Arterioscler. Thromb. Vasc. Biol. 1997; vol. 17(11): pp. 2437-2447; entire document.

Shekhonin, BV et al. Distribution of type I, III, IV and V collagen in normal and atherosclerotic human arterial wall: immunomorphological characteristics. Coll. Relat. Res. 1985; vol. 5: pp. 355-368; entire document.

Siest, G et al. Apolipoprotein E: an important gene and protein to follow in laboratory medicine. Clin. Chem. 1995; vol. 41: pp. 1068-1086; entire document.

Shin, J et al. Vulnerable atherosclerotic plaque: clinical implications. Curr. Vasc. Pharmacol. 2003; vol. 1: pp. 183-204; entire document.

Sondergaard, BC et al. Calcitonin directly attenuates collagen type II degradation by inhibition of matrix metalloproteinase expression and activity in articular chondrocytes. Osteoarthritis Cartilage 2006; vol. 14: pp. 759-768; entire document.

Stary, HC. Composition and classification of human atherosclerotic lesions. Virchows. Arch. A. Pathol. Anat. 1992; vol. 421: pp. 277-290; entire document.

Sundstrom, J et al. Circulating biomarkers of extracellular matrix remodeling and risk of atherosclerotic events. Curr. Opin. Lipidol. 2006; vol. 17: pp. 45-53; entire document.

Talusan, P et al. Analysis of intimal proteoglycans in atherosclerosis-prone and atherosclerosis-resistant human arteries by mass spectrometry. Mol. Cell Proteomics. 2005; vol. 4: pp. 1350-1357; entire document.

Tasheva, ES et al. Differential splicing and alternative polyadenylation generate multiple mimecan mRNA transcripts. J. Biol. Chem. 1997; vol. 272(51): pp. 32551-32556; entire document.

Banks, RE et al. The acute phase protein response in patients receiving subcutaneous IL-6. Clin. Exp. Immunol. 1995; vol. 102: pp. 217-223; entire document.

Terry, JG Apolipoprotein E polymorphism is associated with segment-specific extracranial carotid artery intima-media thickening. Stroke 1996; vol. 27: pp. 1755-1759; entire document.

Tracy, RP et al. Relationship of C-reactive protein to risk of cardiovascular disease in the elderly. Results from the cardiovascular health study and the rural health promotion project. Arterioscler. Thromb. Vasc. Biol. 1997; vol. 17: pp. 1121-1127; entire document.

Turu, MM et al. Intraplaque MMP-8 levels are increased in asymptomatic patients with carotid plaque progression on ultrasound. Atherosclerosis 2006; vol. 187: pp. 161-169; entire document.

Uemura, S et al. Diabetes mellitus enhances vascular matrix metalloproteinase activity: role of oxidative stress. Circ. Res. 2001; vol. 88(12): pp. 1291-1298; entire document.

Veidal, SS et al. Serum markers of liver fibrosis: combining the BIPED classification and the neo-epitope approach in the development of new biomarkers. Dis. Markers 2010; vol. 28: pp. 15-28; entire document.

Venugopal, SK et al. Demonstration that C-reactive protein decreases eNOS expression and bioactivity in human aortic endothelial cells. Circulation 2002; vol. 106: pp. 1439-1441; entire document.

Wagner, WD. Proteoglycan structure and function as related to atherosclerosis. Ann N Y Acad. Sci. 1985; vol. 454: pp. 52-68; entire document.

Wang, TJ et al. Multiple biomarkers for the prediction of first major cardiovascular events and death. New Engl. J. Med. 2006; vol. 355: pp. 2631-2639; entire document.

Whitelock, JM et al. Heparan sulfate: a complex polymer charged with biological activity. Chem. Rev. 2005; vol. 105: pp. 2745-2764; entire document.

Wight, TN et al. The extracellular matrix and atherosclerosis. Curr. Opin. Lipidol. 1995; vol. 6: pp. 326-334; entire document.

Wight, Tn et al. Vascular cell proteoglycans: evidence for metabolic modulation. Ciba Foundation Symposium 124 1986; pp. 241-259; entire document.

Wight, Tn. Versican: a versatile extracellular matrix proteoglycan in cell biology. Curr. Opin. Cell. Biol. 2002; vol. 14: pp. 617-623; entire document.

Wight, Tn et al. Proteoglycans in atherosclerosis and restenosis: key roles for versican. Circ. Res. 2004; vol. 94: pp. 1158-1167; entire document.

Wilson, PWF et al. Apolipoprotein E alleles and risk of coronary disease. a meta-analysis. Arterioscler. Thromb. Vasc. Biol. 1996; vol. 16: pp. 1250-1255; entire document.

Yamada, Y et al. Prediction of the risk of myocardial infarction from polymorphisms in candidate genes. New Engl. J. Med. 2002; vol. 347: pp. 1916-1923; entire document.

Yamada, S et al. Matrix metalloproteinase 12 accelerates the initiation of atherosclerosis and stimulates the progression of fatty streaks to fibrous plaques in transgenic rabbits. Am. J. Pathol. 2008; vol. 172(5): pp. 1419-1429; entire document.

Zwaka, TP et al. C-reactive protein-mediated low density lipoprotein uptake by macrophages: implications for atherosclerosis. Circulation 2001; vol. 103: pp. 1194-1197; entire document.

Zhen, EY et al. Characterisation of metalloprotease cleavage products of human articular cartilage. Arthritis Rheum. 2008; vol. 58(8): pp. 2420-2431; entire document.

Karsdal, MA et al. Novel combinations of post-translational modification neo-epitopes provide tissue-specific biochemical markers—are they the cause or consequence of the disease? Clin. Biochem. 2010; vol. 43: pp. 793-804; entire document.

Mort, JS et al. The use of cleavage site specific antibodies to delineate protein processing and breakdown pathways. J. Clin. Pathol. Mol. Pathol. 1999; vol. 52: pp. 11-18; entire document.

Barascuk, N et al. Development and validation of an enzyme-linked immunosorbent assay for the quantification of a specific MMP-9 mediated degradation fragment of type III collagen-A novel biomarker of atherosclerotic plaque remodelling. Clin. Biochem. 2011; vol. 44: pp. 900-906; entire document.

Arroyo, LH et al. Mechanisms of plaque rupture: mechanical and biologic interactions. Cardiovasc. Res. 1999; vol. 41: pp. 369-375; entire document.

Barascuk, N et al. A novel assay for extracellular matrix remodeling associated with liver fibrosis: An enzyme-linked immunosorbent assay (ELISA) for a MMP-9 proteolytically revealed neo-epitope of type III collagen. Clin. Biochem. 2010; vol. 43; pp. 899-904; entire document.

Bellosta S, et al. Raloxifene inhibits matrix metalloproteinases expression and activity in macrophages and smooth muscle cells. Pharmacol. Res. 2007; vol. 56: pp. 160-167; entire document.

(56) References Cited

OTHER PUBLICATIONS

Bobryshev, YV. Calcification of elastic fibers in human atherosclerotic plaque. Atherosclerosis 2005; vol. 180: pp. 293-303; entire document.
Brown, DC et al. Characteristics of the in vitro interaction of a small proteoglycan (PG II) of bovine tendon with type I collagen. Matrix 1989; vol. 9: pp. 468-478; entire document.
Cattin L, et al. Polymorphism of the apolipoprotein E gene and early carotid atherosclerosis defined by ultrasonography in asymptomatic adults. Arterioscler. Thromb. Vasc. Biol. 1997; vol. 17: pp. 91-94; entire document.
Chapman, HA et al. Emerging roles for cysteine proteases in human biology. Annu. Rev. Physiol. 1997; vol. 59: pp. 63-88; entire document.
Clarkson, TB et al. Stage of reproductive life, atherosclerosis progression and estrogen effects on coronary artery atherosclerosis, In: Lobo RA, editor. Treatment of the Postmenopausal Woman: Basic and Clinical Aspects, 3 ed. San Diego: Elsevier; 2007. p. 509-528.
Death, AK et al. High glucose alters matrix metalloproteinase expression in two key vascular cells: potential impact on atherosclerosis in diabetes. Atherosclerosis 2003; vol. 168: pp. 263-269; entire document.
Dours-Zimmermann, MT et al. A novel glycosaminoglycan attachment domain identified in two alternative splice variants of human versican. J. Biol. Chem. 1994: vol. 269: pp. 32992-32998; entire document.
Danielson, KG et al. Targeted disruption of decorin leads to abnormal collagen fibril morphology and skin fragility. J. Cell Biol. 1997; vol. 136: pp. 729-743; entire document.
Eriksen, HA et al. Type I and type III collagen synthesis and composition in the valve matrix in aortic valve stenosis. Atherosclerosis 2006; vol. 189: pp. 91-98; entire document.
Evanko, SP et al. Proteoglycan distribution in lesions of atherosclerosis depends on lesion severity, structural characteristics, and the proximity of platelet-derived growth factor and transforming growth factor-beta. Am. J. Pathol. 1998; vol. 152: pp. 533-546; entire document.
Funderburgh, JL. Keratan sulfate: structure, biosynthesis, and function. Glycobiology 2000; vol. 10: pp. 951-58; entire document.
Funderburgh, JL et al. Macrophage receptors for lumican. A corneal keratan sulfate proteoglycan. Invest. Ophthalmol. Vis. Sci. 1997; vol. 38: pp. 1159-1167; entire document.
Funderburgh, JL et al. Mimecan, the 25-kDa corneal keratan sulfate proteoglycan, is a product of the gene producing osteoglycin. J. Biol. Chem. 1997; vol. 272(44): pp. 28089-28095; entire document.
Gabay, C et al. Acute-phase proteins and other systemic responses to inflammation. New Engl. J. Med. 1999; vol. 340(6): pp. 448-454; entire document.
Garcia-Touchard, A et al. Extracellular proteases in atherosclerosis and restenosis. Arterioscler. Thromb. Vasc. Biol. 2005; vol. 25: pp. 1119-1127; entire document.
Gardner, CD et al. Association of small low-density lipoprotein particles with the incidence of coronary artery disease in men and women. JAMA 1996; vol. 276: pp. 875-881; entire document.
Garrone, R et al. Distribution of minor collagens during skin development. Microsc. Res. Tech. 1997; vol. 38: pp. 407-412; entire document.
Gefter ML, et al. A simple method for polyethylene glycol-promoted hybridization of mouse myeloma cells. Somatic Cell Genet. 1977; vol. 3(2): pp. 231-236; entire document.
Graham I, et al. European guidelines on cardiovascular disease prevention in clinical practice: executive summary. Eur. Heart J. 2007; vol. 28: pp. 2375-2414; entire document.
Halpert, I et al. Matrilysin is expressed by lipid-laden macrophages at sites of potential rupture in atherosclerotic lesions and localizes to areas of versican deposition, a proteoglycan substrate for the enzyme. Proc. Natl. Acad. Sci. USA 1996; vol. 93: pp. 9748-9753; entire document.
Haraki T, et al. Carotid artery intima-media thickness and brachial artery flow-mediated vasodilation in asymptomatic Japanese male subjects amongst apolipoprotein E phenotypes. J. Intern. Med. 2002; vol. 252: pp. 114-120; entire document.
Hatanaka, K et al. Immunohistochemical localization of C-reactive protein-binding sites in human atherosclerotic aortic lesions by a modified streptavidin-biotin-staining method. Pathol. Int. 1995; vol. 45: pp. 635-641; entire document.
Heegaard, AM et al. Biglycan deficiency causes spontaneous aortic dissection and rupture in mice. Circulation 2007; vol. 115: pp. 2731-2738; entire document.
Herman, MP et al. Expression of neutrophil collagenase (matrix metalloproteinase-8) in human atheroma: a novel collagenolytic pathway suggested by transcriptional profiling. Circulation 2001; vol. 104: pp. 1899-1904; entire document.
Host, NB et al. The aminoterminal propeptide of type III procollagen provides new information on prognosis after acute myocardial infarction. Am. J. Cardiol. 1995; vol. 76: pp. 869-873; entire document.
Jeppesen, J et al. High triglycerides/low high-density lipoprotein cholesterol, ischemic electrocardiogram changes, and risk of ischemic heart disease. Am. Heart. J. 2003; vol. 145: pp. 103-108.
Johnson, JL Matrix metalloproteinases: influence on smooth muscle cells and atherosclerotic plaque stability. Expert Rev. Cardiovasc. Ther. 2007; vol., 5(2): pp. 265-282.
Kampmann, A et al. The proteoglycan osteoglycin/mimecan is correlated with arteriogenesis. Mol. Cell. Biochem. 2009; vol. 322: pp. 15-23; entire document.
Karsdal, MA et al. Biochemical markers and the FDA Critical Path: how biomarkers may contribute to the understanding of pathophysiology and provide unique and necessary tools for drug development. Biomarkers 2009; vol. 14(3): pp. 181-202; entire document.
Karsdal, MA et al. Tibolone inhibits bone resorption without secondary positive effects on cartilage degradation. BMC Musculoskelet. Disord. 2008; vol. 9: p. 153; entire document.
Katsuda, S et al. Atherosclerosis and extracellular matrix. J. Atheroscler. Thromb. 2003; vol. 10(5): pp. 267-274; entire document.
Knox, SM et al. Perlecan: how does one molecule do so many things? Cell. Mol. Life Sci. 2006; vol. 63.21: pp. 2435-2445; entire document.
Koenig, W et al. Biomarkers of atherosclerotic plaque instability and rupture. Arterioscler. Thromb. Vasc. Biol. 2007; vol. 27: pp. 15-26; entire document.
Kragel, AH et al. Morphometric analysis of the composition of atherosclerotic plaques in the four major epicardial coronary arteries in acute myocardial infarction and in sudden coronary death. Circulation 1989; vol. 80(6): pp. 1747-1756; entire document.
Kuller, LH et al. Relation of C-reactive protein and coronary heart disease in the MRFIT nested case-control study. Am. J. Epidemiol. 1996; vol. 144(6): pp. 537-547; entire document.
Kunz J. Matrix metalloproteinases and atherogenesis in dependence of age. Gerontology 2007; vol. 53: pp. 63-73; entire document.
Kuzuya, M et al. Effect of MMP-2 deficiency on atherosclerotic lesion formation in apoE-deficient mice. Arterioscler. Thromb. Vasc. Biol. 2006; vol. 26: pp. 1120-1125; entire document.
Lauer-Fields, JL et al. Matrix metalloproteinases and collagen catabolism. Biopolymers 2002; vol. 66: pp. 19-32; entire document.
Lawrie, TD et al. Serum fatty-acid patterns in coronary-artery disease. Lancet 1961; vol. 1: pp. 421-424; entire document.
Leinonen, M et al. Evidence for infectious agents in cardiovascular disease and atherosclerosis. Lancet Infect. Dis. 2002; vol. 2: pp. 11-17; entire document.
Liu, J et al. Lysosomal cysteine proteases in atherosclerosis. Arterioscler. Thromb. Vasc. Biol 2004; vol. 24: pp. 1359-1366; entire document.
Lutgens, SPM et al. Cathepsin cysteine proteases in cardiovascular disease. FASEB J. 2007; vol. 21: pp. 3029-3041; entire document.
Luttun, A et al. Loss of matrix metalloproteinase-9 or matrix metalloproteinase-12 protects apolipoprotein E-deficient mice

(56) References Cited

OTHER PUBLICATIONS against atherosclerotic media destruction but differentially affects plaque growth. Circulation 2004; vol. 109: pp. 1408-1414; entire document.

Fernández B, Kampmann A, Pipp F, Zimmermann R, Schaper W., Osteoglycin expression and localization in rabbit issues and atherosclerotic plaques. Molecular and Cellular Biochemistry, 2003, 246:3-11.

* cited by examiner

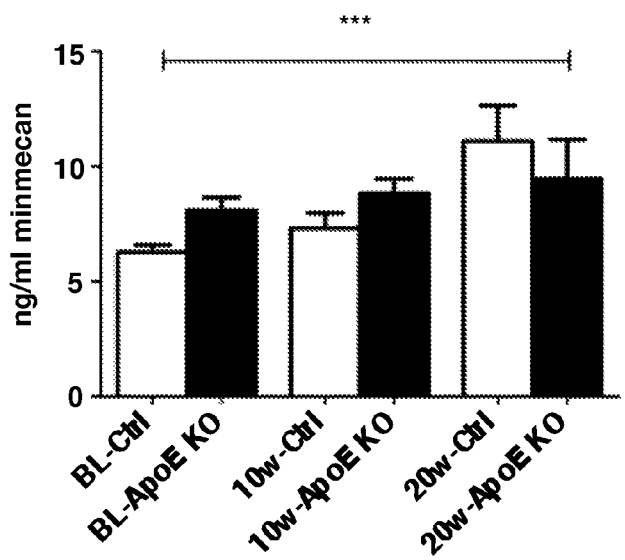
FIG. 3A
FIG. 3B
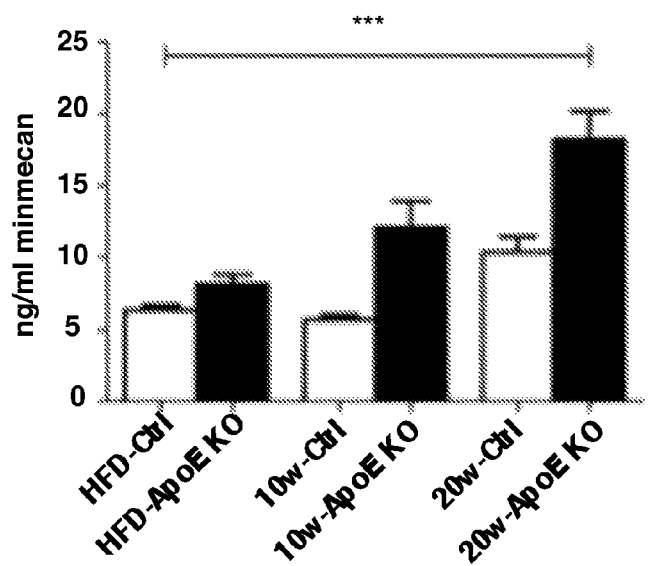
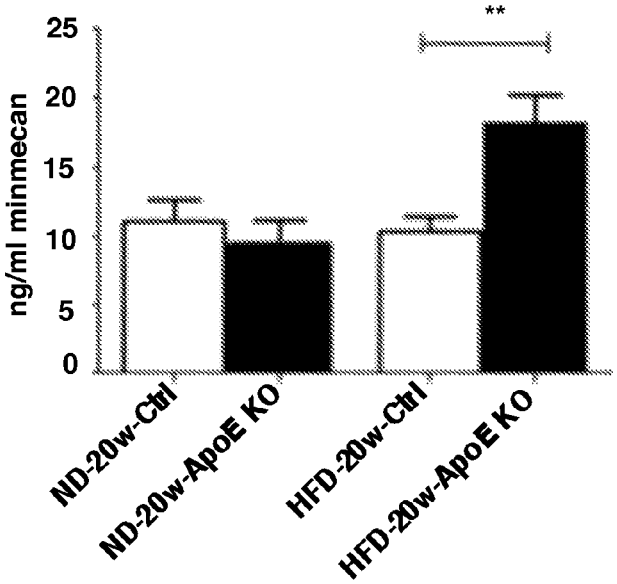
FIG. 3C

BIOCHEMICAL MARKERS FOR CVD RISK ASSESSMENT

The present invention relates to assays for detection of biochemical markers valuable for diagnostic purposes in cardiovascular disease and prognosis of disease development, including biochemical markers indicative of the risk of cardiovascular events resulting from atherosclerotic development and plaque instability.

Worldwide, cardiovascular disease (CVD) is the leading cause of morbidity and mortality. At present, there are no effective and non-invasive diagnostic methods that allow for diagnosis and classification of patients into different risk-groups and for the diagnosis of low risk patients. Diagnostic and prognostic tools are composed mainly of multivariate analysis of simple markers, such as age, smoking and various lipid and lipoprotein concentrations.

CVD covers several clinical syndromes, primarily, angina pectoris, myocardial infarction (coronary thrombosis) and stroke. All of these syndromes are usually the sequelae of complicated atherosclerosis.

Atherosclerosis begins with intimal thickening in childhood and progresses to fatty streaks in the intima of arteries—these lesions are characterized as type I and II, respectively. Fatty streaks are the earliest macroscopically visible lesions in the development of atherosclerosis and occur among almost all human beings of all races and societies. In the non-pathogenic state, endothelial cells (EC) resist adhesive interactions with leukocytes. However, the actions of proinflammatory cytokines and accumulated oxidized lipoprotein in the arterial wall during atherogenesis, initiate expression of adhesion molecules, such as intercellular adhesion molecules (ICAM)-1 and vascular cell adhesion molecules (VCAM)-1, on the surface of aortic ECs. This allows for capturing and transmigration of leukocytes through the endothelial surface, into the intimal part of the vessel wall. The development of plaques involves an increasing number of smooth muscle cells (SMC) that undergo displacement and apoptosis, which results in increased matrix turnover. The impaired collagen synthesis can result in a weakened fibrous cap and an atherosclerotic plaque that is more prone to rupture; however, most investigators believe that the actions of a proteolytic enzymes such as matrix metallo-proteases (MMPs) and other proteases importantly contribute to the risk of plaque rupture (Clarkson and Kaplan 509-28).

Plaques are divisible into two different types: 'vulnerable' and 'stabilized' plaques. However, for detailed histological analyses and molecular understanding, a more detailed classification is often used. There are three major stages in development of plaque: initiation, fatty streaks and the complex/advanced plaque (Stary H. C.).

Atherosclerotic plaques develop within the intima of arteries, and may be classified depending on their composition and structure. This classification divides lesions into eight types (Stary H. C.):

I. Macrophages loaded with and enlarged by lipid droplets (macrophage foam cells) are increased in the intima.

II. Macrophage foam cells accumulate in the deep part of the proteoglycan layer along with lipid droplets within the intimal SMC. The layers of foam cells are visible as fatty streaks. In type II lesions monocytes penetrate the endothelial lining by monocyte chemo attractant proteins (mainly MCP-1), which are over expressed in human atheroma. The early types of lesion (type I and II) can start in infancy and do not necessarily lead to plaque rupture. Furthermore, the development of atherosclerosis may end after the formation of type III lesion, and the formation of plaque is not predictable (Stary H. C.).

III. The type III lesion is determined as the intermediate lesion between the fatty streaks (type II) and the atheroma (type IV). These lesions contain pools of extracellular lipid and thereby expand the spaces between the normally closely adjoining SMCs of the deep musculo-elastic layer of the intima. The pools of material may replace proteoglycans and collagen fibres that normally reside here, but this occurs with little impact at this stage of atherogenesis.

IV. The atheroma is the first clinical sign of atherosclerosis. Displacement of SMCs in the intima of arteries by accumulating extracellular pools of lipids and disruption of the intimal architecture is a hallmark of a type IV lesion. The formation of the lipid cores is the end result of this SMC displacement. Formation of a lipid core accounts for the increased wall thickening. The lipid core is a large and well delineated region of the deep intima where the normal structural elements of this part of the arterial wall have been replaced by densely packed foam cell remnants, free lipids droplets, cholesterol crystals and calcium particles. SMCs normally resident in this area are decreased or completely absent at this stage of atherosclerosis progression. Any remnant SMCs become widely dispersed and have developed elongated cell bodies and very often unusually thick basement membranes. At this stage, the development of a layer overlying the lipid core begins. This layer consists of collagen and proteoglycan-rich intercellular matrix, SMCs with and without lipid droplets, macrophages, and foam cells.

V. The response to type IV lesion is the formation of a reparative fibrous tissue matrix, forming a fibrous "cap". Typically, these lesions will consist of layers of lipid cores and reparative tissue irregularly stacked on top of each other. Events such as hematoma and thrombus formation may additionally complicate these types of lesions. If not fatal, these lesion complications are integrated into the lesion and overgrown by a thin layer of reparative matrix tissue, consisting of collagens and proteoglycans. The content of extracellular matrix proteins collagen and proteoglycans increases in the atherosclerotic plaque during formation of the cap.

VI. The defects of the endothelium such as fissures, erosions, ulcerations, hematoma, thrombus, haemorrhage can if combined lead to more complicated lesion type designated type VI lesion.

VII. The lesion is often referred to as calcified lesion, where more than 50% of the lesion consists of mineral. In addition to calcifications, these lesions contain abundance of reparative fibrous connective tissue. When the SMCs trapped in this undergo apoptosis and disintegrate; their mineralized organelles become a part of the calcification.

VIII. The fibrotic lesion follows the calcific lesion. The fibrotic lesion may consist entirely of collagen and no lipid. (Stary H. C.)

Cardiovascular events are often the result of plaque rupture, in which inflammation and the release of proteases weaken the shoulder regions of the fibrous cap and allow the fatty materials in the plaque to come into contact with the blood precipitating a mural thrombus (Clarkson and Kaplan). Thinning of the fibrous cap by increased protease activity in the combination with decreased matrix production, is considered a hallmark of plaque instability increasing the risk of rupture. Vulnerability of plaques and their risk of rupture is an area of clinical interest. Definition of a vulnerable plaque (VP) is not standardized, but there is a general agreement stating existence of three histological hallmarks compared to stable plaque:
 1) A larger lipid core (>40 percent of total lesion).
 2) A thinner fibrous cap (65-150 micrometers).
 3) Large amount of acute inflammatory cells.

Major criteria for defining VP include: active inflammation (presence of monocytes, macrophages and T cells), thin cap with large lipid core, endothelial denudation with superficial platelet aggregation, fissured plaque, and >90% stenosis of the artery. Other minor criteria include: superficial calcified nodule, intraplaque haemorrhage, endothelial dysfunction, and outward remodelling (Shin, Edelberg, and Hong).

Plaque complications, instability and rupture may be inhibited by medical treatment and/or lifestyle modification. In some cases, however, more invasive methods may be needed, i.e. angioplasty or bypass surgery.

Presently, diagnostic tools are based on either static image analyses still under development or low-technology methods such as systolic and diastolic blood pressure levels related to the risk of CVD. The field has devoted much attention to the development of multivariate analysis that may better identify patients at high risk. One such model is the SCORE-model (Systematic Coronary Risk Evaluation model). In 1994, with a revision in 2003, The European Atherosclerosis Society, The European Society of Cardiology and The European Society of Hypertension issued a set of recommendations regarding prevention of coronary heart diseases. This guideline is based on several assessment techniques, which have been developed to assess the risk of CVD in asymptomatic subjects, i.e. identification of asymptomatic high-risk patients. The SCORE-model integrates gender, age, smoking, systolic blood pressure and either total cholesterol or the cholesterol/HDL ratio as risk factors (Graham et al.).

In order to make a more detailed diagnosis, the SCORE model is not sufficient and imaging techniques are used. Imaging methods are therefore used mostly on patients in the high-risk group or during research.

Imaging Techniques

Coronary angiography (CAG) is currently the gold standard imaging technique for defining the degree of stenosis. CAG images the lumen of the vessel in two dimensions, but is restricted only to the lumen and not the vessel wall thereby CAG can not distinguish between an artery with a stable plaque and an artery with a vulnerable plaque. CAG is often used to determine whether a patient needs surgery; angioplasty or bypass. In order to determine if a point of luminal narrowing is an advanced plaque, other techniques are needed i.e. intravascular coronary ultrasound (IVUS) or angioscopy.

IVUS provides two-dimensional cross-sectional images of the plaque and vessel wall, and is considered as a method good for characterization of vessel wall and morphology and the degree of calcification, but poor for assessing the lipids in the lesion. However, IVUS is invasive and requires expertise and expense: therefore, its use is not wide spread. Angioscopy is another useful method in understanding and identifying atherosclerosis. Angioscopy is a direct visualization of plaque surface and has the capability of detecting colour of plaque and thrombosis. Angioscopy is, however, invasive and technically difficult, and so far it is has not been able to detect the degree of plaque extension. Another imaging technique that currently is receiving much attention is Magnetic Resonance imaging (MRI). MRI is non-invasive and able to identify carotid plaque at high risk of stroke. On the other hand, MRI is not the best technique to image coronary arteries, because of small plaque sizes and location of the coronary arteries. Other imaging techniques are under development, i.e. elastography, thermography and optical coherence tomography (Schaar et al.).

The imaging techniques mentioned are all under development and alone, none can identify a vulnerable plaque, but they are useful tools in understanding both the molecular events and plaque turnover prior to rupture. Presently, the only opportunity to diagnose CVD at an early stage is to utilize a range of risk factors for established coronary heart disease, peripheral artery disease and cerebrovascular atherosclerotic disease of the patient in question, as well as close relatives of the patient.

Present Biochemical Markers

At present, several biochemical markers are known as risk factors for atherosclerosis. Recently much attention has been directed to the measurement of biochemical marker concentrations in serum; both lipids such as total cholesterol, low-density lipoprotein cholesterol (LDL-C) and the high-density lipoprotein cholesterol (HDL-C) and inflammatory markers such as C-Reactive Protein (CRP), Interleukin-6 (IL-6), Interleukin-18 (IL-18), Tumor Necrosis Factor-alpha (TNFα), CD40, CD40 ligand (CD40L) and others.

Among lipoprotein markers, there have been at least two noteworthy advances. The size of LDL particles seems to predict the degree of atherosclerosis progression. Increased concentrations of small LDL particles are more related to CVD risk than increased concentrations of large particles (Gardner, Fortmann, and Krauss).

The level of HDL-C is strongly related to triglyceride, and high triglyceride level is correlated to a higher risk of CHD. A cohort study by Jeppesen et al. (2003) found high TG/low HDL-C as the strongest risk factors of IHD (ischemic heart disease)(Jeppesen et al.).

Lipid profiles are important for evaluation of risk factors, but do not allow understanding and measurement of the molecular events associated with plaque turnover. A number of biochemical markers have been suggested as risk factors for CVD, although not specific product of the disease. These include CRP and Bone natriuretic peptide (BNP) (see Table 1). Table 1 summarizes some of the known markers of CVD.

TABLE 1

A selection of present biochemical markers in CVD.

| Marker | Type | Description |
| --- | --- | --- |
| C-reactive protein (CRP) | Inflammatory | Produced in the liver, increases during inflammatory states. |
| Pregnancy-associated plasma protein (PAPP-A) | Inflammatory | Zinc-binding protein that acts as an enzyme, specifically a metallopeptidase. |
| Interleukin-6 (IL-6) | Inflammatory cytokine | Elevated level in heart failure and myocardial infarction. |
| Inteleukin-8 (IL-8) | Inflammatory cytokine | Elevated in myocardial infarctions. |
| Interleukin-18 | Inflammatory cytokine | Elevated in myocardial infarction. |
| TNF-α (Tumor Necrosis Factor) | Cytokine | Conc. Elevated in the settings of heart failure. |
| MCP-1 | Chemokine | Recruits monocytes from the blood into early atherosclerotic lesion. |

TABLE 1-continued

A selection of present biochemical markers in CVD.

| Marker | Type | Description |
|---|---|---|
| Intercellular adhesion molecule-1 (ICAM-1) | Adhesion molecule | Elevated in myocardial infarctions and stroke. |
| Vascular cellular adhesion molecule-1 (VCAM-1) | Adhesion molecule | Elevated in myocardial infarctions and stroke. |
| Brain natriuretic peptide (BNP) | Neurohormonal activity | Produced in atria and ventricles of normal healthy heart. |
| Lipoprotein-associated phospholipase A2 (Lp-PLA$_2$) | Phospholipase | LDL-associated Lp-PLA$_2$ has proatherogenic effects. |
| Creatine phospokinase (CK-MB) | Enzyme | Useful as early detection of myocardial infarction. |
| Myeloperoxidase (MPO) | Heme enzyme | Activates metalloproteases and promotes destabilization of plaque. |
| Myoglobulin | Heme protein | Released upon tissue necrosis. |
| CD40L | Protein | Released in the early stages of atherogenesis through to plaque rupture. Elevated in stroke. |
| Troponin T (TnT) | Protein | Tool for risk stratification. |
| Heart-Type Fatty Acid-binding protein (H-FABP) | Protein | H-FARB is released from the heart immediately after infarction. |
| Microalbuminurea | Protein | Marker of vascular endothelial dysfunction. |
| Low density lipoprotein cholesterol (LDL-C) | Lipoprotein | Transport cholesterol in the blood. |
| High Density lipoprotein cholersterol (HDL-C) | Lipoprotein | Holds antioxidant and antiinflammatory properties. |
| Triglyceride | Lipid | |
| PIIINP | Procollagen | Marker of type III collagen turnover. |

Thus, a range of different biochemical markers have been suggested as markers of cardiovascular events. Wang et al (2006) have measured 10 different biochemical markers in 3200 patients participating in the Framingham study, described in Tabel 1. The conclusion was that the measurement of 10 biochemical markers only contributes moderately to diagnosis over and above standard risk factors. Of the 10 biochemical markers, B-type natriuretic peptide level, C-reactive protein level and the urinary albumin-to-creatinine ratio showed the best correlation between marker and death/cardiovascular events (Wang et al.).

Mimecan

Recently, a proteoglycan mimecan, also known as osteoglycin (OGN) has been implicated in regulation of collagen fibrillogenesis, artheriogenesis and in regulation of left ventricular mass[12-14]. Mimecan/OGN is part of the small leucin-rich proteoglycans (SLRP). Other members of this family are biglycan, decorin, fibromodulin and lumican. SLRPs comprise many important functions such as regulation of matrix structure, cell cycle and growth actions evoking multiple signaling pathways. The SLRPs modulate cell-matrix interactions and cell function, without participating in structural scaffold of the ECM.

The atherosclerotic plaque is continuously remodeling, thereby releasing a range of degradation products of ECM proteins, the so called neoepitopes[15]. These neoepitopes may be specific for the tissue of origin and are therefore interesting when designing novel molecular biochemical markers. The neoepitope based biochemical markers measurable in urine and serum are receiving increased attention for their diagnostic and prognostic potential[16].

Matrix Metalloproteinases (MMP)

MMP is a large group of endopeptidases, capable of degrading most components of the ECM. Presently, more than 25 MMPs have been identified. Metallo-proteinases are characterized by an active site containing a metal atom, typically zinc, and are secreted as zymogens. Specific tissue inhibitors, TIMPs, regulate the activity of MMPs. A great variety of MMPs are found in the atherosclerotic plaques. They are most often located in macrophages bordering the fibrous cap, within plaque shoulders in SMC and macrophages and are rarely identified within the fibrous cap (Kunz J.).]

MMPs are classified in different groups according to their substrate specificity: Collagenases, which degrade fibrillar collagen, like collagen type I, II, III and V but also proteoglycans; Gelatinases, which degrade proteoglycans, collagen type IV, V, VII and elastin; Stromelysin that is active against proteoglycans and elastin (Rouis M). These three subgroups are of particular interest with regards to matrix remodelling in atherosclerotic plaques.

Gelatinases

Insoluble elastin is digested by MMP-2 and -9, both belonging to the gelatinase-family of MMPs. MMP-9 has an important role affecting the size and composition of atherosclerotic plaque. In unstable human atherosclerotic plaques and in vulnerable regions of plaques, greater expression and concentration of MMP-9 have been observed. Moreover, MMP-9 is found intracellularly (indicating active synthesis) in coronary plaques more often in patients with unstable angina compared with those with stable angina. Blood MMP-9 level increases in association with coronary atherosclerosis and predicts adverse cardiovascular events (Sundstrom and Vasan). A recent study by Kuzuya et al (2006) indicates that MMP-2 is responsible for accumulation of SMC in the fibrous cap and thereby inducing plaque instability.

Stromelysin

MMP-3 belongs to the stromelysin proteases and is capable of degrading both elastin and proteoglycans. A study by Yamada et al (2002) indicates that MMP-3 may prove to be a reliable mean of predicting the genetic risk of myocardial infarction in women.

Collagenases

MMP-1, -8 and -13 have all been identified in atherosclerotic plaques where they degrade proteoglycans and collagen types I and III.

MMP-1, -8 and -13 are collagenases, which cleave collagen into two fragments that are further degraded by MMP-2, -3 or -9.

MMP-8 is expressed by neutrophils, not commonly found in human atheroma but has been identified in atherosclerotic plaques. MMP-8 may be partly responsible for degradation of the fibrous cap as MMP-8 has a preference for collagen type I (Herman et al), having a three fold greater activity in degradation of collagen I than MMP-1 and 13. This is supported by Turu et al (2006), in this study the content of MMP-8 in the plasma are significantly higher for patients with vulnerable plaques, than patients with stable plaques.

MMP-13 has been reported to cleave SLRPS, with high specificity for biglycan. Degradation of biglycan by MMP-13 at a specific cleavage site ( . . . $G_{177}/V_{178}$) has previously been demonstrated by Monfort et al. (2005) and proposed to play a important role in early detection of cartilage degradation in osteoarthritis.)

Cathepsins

Human cysteine cathepsins consist of 11 members, including cathepsins B, K, L, and S, and are predominantly expressed within the endosomal/lysosomal compartments of cells. Cathepsins are capable of catalysing the hydrolytic breakdown of proteoglycans, collagen and elastin.

In abdominal aortic aneurysm (AAA) high levels of cathepsins S, K, and L were found compared to normal aorta. Normal human vascular SMC contain no detectable cathepsin K by immunostaining, but cells within atherosclerotic plaques are clearly positive. Cathepsin K is localized in rupture-prone areas such as the fibrous cap, plaque shoulders and at the actual site of plaque ruptures (Chapman et al). Cathepsin S is found to co-localize with regions of increased elastin breakdown in atherosclerotic plaques, and reduced atherosclerosis is observed in cathepsin S- and K-deficient mice (Liu et al).

Both cathepsin L and K degrade several proteoglycans and collagen type I and II, cathepsin K degrades within covalently cross-linked triple helices, while cathepsin L cleaves only in the nonhelical telopeptide regions. Cathepsin K is localized in the fibrous cap and plaque shoulder. Cathepsin K expression in normal arteries is very low. Early human atherosclerotic lesions showed cathepsin K expression in the intimal and medial SMCs. In advanced atherosclerotic plaques, cathepsin K was localized mainly in macrophages and SMCs of the fibrous cap (Lutgens et al). Cathepsin K protein levels were increased in atherosclerotic lesions when compared with normal arteries, whereas cathepsin K mRNA levels were similar in both atherosclerotic and normal arteries. Furthermore, it was shown that cathepsin K mRNA and protein levels were highest in advanced but stable human atherosclerotic plaques compared with early atherosclerotic lesions and lesions containing thrombus (Chapman et al).

Cathepsin S is only sparsely expressed in intimal and medial SMCs in early human atherosclerotic lesion and fatty streaks. In advanced human atherosclerotic plaques cathepsin S was localized in macrophages and SMCs of the fibrous cap. EC lining the lumen of the vessel itself and the plaque microvessels also expressed cathepsin S. Furthermore, cathepsin S mRNA and protein levels were increased in human atheroma compared with normal arteries (Lutgens et al). Cathepsin S can degrade proteoglycans, elastin and collagen (Liu et al).

Presently, the determination of CVD risk is occurring at a late stage in atherosclerosis progression; a point in which there is a significant risk of fibrous plaque rupture. There is a need for diagnostic or prognostic assays that will provide information regarding atherosclerosis or CVD risk at both earlier stage and late stages. The findings of Katsuda et al (1992) suggest that there are enzymatic mechanisms for removal of collagens from advanced lesions, suggesting indeed a major role of neo-epitopes in arteriosclerosis.

The present invention provides a method of bioassay for the quantification of peptide fragments comprising a neo-epitope formed by cleavage of a protein of an atherosclerotic plaque by a proteinase, said method comprising contacting a sample comprising said peptide fragments with an immunological binding partner having specific binding affinity for a said neo-epitope and determining the level of binding of said immunological binding partner to peptide fragments in said sample, wherein said protein is mimecan.

The result of said assay may produce an index indicative of the degree of risk in a particular patient of rupture of an atherosclerotic plaque or of the vulnerable status of the atherosclerotic plaques of a patient.

Patients having a value for said index above a threshold level may be recommended for further investigation by plaque imaging methods (including those discussed above) or for the prescribing of medication for treatment of atherosclerosis or for surgical treatment of atherosclerosis, and such follow up investigations or treatment may form part of the method of the invention.

Said immunological binding partner may have specific binding affinity for peptide fragments comprising a C-terminal neo-epitope or an N-terminal neo-epitope.

The immunological binding partner may be one specifically reactive with a C-terminal or N-terminal neo-epitope formed by cleavage of mimecan.

An immunological binding partner may be considered to be specifically reactive with a neo-epitope if it is reactive with peptides terminating in the neo-epitope sequence but is not substantially reactive with intact mimecan and is not specifically reactive with peptides in which the neo-epitope terminal sequence is extended by one or more further amino acids.

Preferably, the immunological binding partner has specific binding affinity for a peptide fragment which comprises a neo-epitope formed by cleavage of mimecan by one or more proteases giving any one of the following peptide fragments originating from mimecan;

```
DFADIPNLR              SEQ ID NO 1

TGNLIEDIEDGTFSK        SEQ ID NO 2

LDFTGNLIEDIEDGTFSK     SEQ ID NO 3

LEGNPIVLGK             SEQ ID NO 4

RLDFTGNLIEDIEDGT       SEQ ID NO 5

RLDFTGNLIEDIEDGTFSK    SEQ ID NO 6

RLEGNPIVLGK            SEQ ID NO 7

DFTGNLIEDIEDGTFSK      SEQ ID NO 8

DHNALESVPLNLPESLR      SEQ ID NO 9

DIDAVPPLPK             SEQ ID NO 10

FTGNLIEDIEDGTFSK       SEQ ID NO 11

GNLIEDIEDGTFSK         SEQ ID NO 12
```

Suitable immunological binding partners may therefore be specifically reactive with any of the following sequences consisting of six amino acids (or more) at the N terminal of a peptide:

```
DFADIP . . .           SEQ ID NO 13

TGNLIE . . .           SEQ ID NO 14

LDFTGN . . .           SEQ ID NO 15

RLDFTG . . .           SEQ ID NO 16

RLEGNP . . .           SEQ ID NO 17

DFTGNL . . .           SEQ ID NO 18
```

```
DHNALE . . .          SEQ ID NO 19

DIDAVP . . .          SEQ ID NO 20

FTGNLI . . .          SEQ ID NO 21

GNLIED . . .          SEQ ID NO 22
``` or with any of the following sequences consisting of six amino acids (or more) at the C-terminal of a peptide:

```
. . . DIPNLR          SEQ ID NO 23

. . . DGTFSK          SEQ ID NO 24

. . . PIVLGK          SEQ ID NO 25

. . . DIEDGT          SEQ ID NO 26
```

Further cleavage sites defining neo-epitopes that may be assayed in a similar manner can be identified by exposing mimecan to any of the enzymes described herein and isolating and sequencing peptides thereby produced.

Optionally, said immunological binding partner has specific binding affinity for the sequence EDIEDGTFSK [SEQ ID NO 28] at the C terminal of a peptide or has specific binding affinity for the sequence TGNLIEDIED [SEQ ID NO 30] at the N terminal of a peptide.

Assays for more than one of the peptides described above may be conducted separately and their results combined or more than one of the peptides described above may be measured together.

The result of an assay according to the invention may be combined with one or more other measured biomarkers to form a composite index of diagnostic or prognostic value.

The term 'immunological binding partner' as used herein includes polyclonal and monoclonal antibodies and also specific binding fragments of antibodies such as Fab or F(ab')$_2$. Thus, said immunological binding partner may be a monoclonal antibody or a fragment of a monoclonal antibody having specific binding affinity.

The term 'protein' used herein includes lipoproteins and proteoglycans and other protein-(non-protein) naturally occurring conjugates.

Generally, all previously known immunoassay formats can be used in accordance with this invention including heterogeneous and homogeneous formats, sandwich assays, competition assays, enzyme linked assays, radio-immune assays and the like. Thus, optionally, said method is conducted as a competition immunoassay in which said immunological binding partner and a competition agent are incubated in the presence of said sample and the competition agent competes with the peptide fragments in the sample to bind to the immunological binding partner.

Said competition agent may be a synthetic peptide or a purified native peptide formed by cleavage of mimecan.

Alternatively, said method is conducted as a sandwich immunoassay in which said immunological binding partner and a further immunological binding partner having specific binding affinity for a peptide sequence contained in peptide fragments bound by said immunological binding partner are incubated in the presence of said sample and both bind together to said peptide fragments in the sample. Suitably, in such a format, a first antibody binds the sequence EDIEDGTFSK and a second antibody binds the sequence TGNLIEDIED [SEQ ID NO 30].

One suitable method could be a competition immunoassay using monoclonal antibodies or antibody binding fragments binding to neo-epitopes of fragments of mimecan. Appropriately selected synthetic peptides coated onto the solid surface of a microtitre plate could compete with the sample for binding to the monoclonal antibodies or binding fragments. Alternatively, purified, native fragments from one or more of these proteins carrying the neo-epitope recognised by the monoclonal antibody or binding fragment could be used on the solid surface. Yet another alternative is to immobilise the monoclonal antibody or binding fragment on the solid surface and then co-incubate the sample with a synthetic peptide appropriately linked to a signal molecule, e.g. horseradish peroxidase or biotin. The sample may be a sample of urine, serum, blood, plasma or other, e.g. atherosclerotic plaque biopsy.

In certain preferred methods, the sample is a patient derived sample, and the method further comprises comparing the determined level of said binding of said peptide fragments with values characteristic of (a) comparable healthy individuals and/or (b) a pathological atherosclerotic condition and optionally associating a higher level of the measured peptide (normally indicated by a higher level of binding) with a more severe degree of a said condition.

An aspect of the present invention relates to the development of monoclonal antibodies recognising neo-epitopes as described above. This can be achieved by immunising mice with synthetic peptides originating from the amino acid sequence of mimecan (including the sequences listed above or sequences terminating therein), fusing the spleen-cells from selected mice to myeloma cells, and testing the monoclonal antibodies for binding to neo-epitopes on relevant synthetic peptides. Specificity for neo-epitopes can be ensured by requiring reactivity with a synthetic peptide and a lack of reactivity with either a C-terminal prolonged form of the immunising peptide (for a C-terminal neo-epitope) or an N-terminal prolonged form of the immunising peptide (for an N-terminal neo-epitope). Antibodies for neo-epitopes may also be evaluated to establish a lack of binding capacity to the intact protein. Alternatively, specificity for a neo-epitope can be ensured by requiring the reactivity of the antibody to be negatively dependent on the presence of biotin or other functional groups covalently linked to one of the terminal amino acids.

The invention includes an immunological binding partner which is specifically immunoreactive with a neo-epitope formed by cleavage of mimecan by a protease at an end-site in any one of the partial sequences set out above, and may be for instance a monoclonal antibody or a binding fragment thereof.

The invention includes a cell line producing a monoclonal antibody against a C-terminal or N-terminal neo-epitope formed by cleavage of mimecan at the end-sites of sequences in any one of the partial sequences set out above.

The invention further provides a peptide comprising a C-terminal or N-terminal neo-epitope formed by cleavage of mimecan in any one of the partial sequences set out above. Such a peptide may be conjugated as a hapten to a carrier for producing an immune response to said peptide, or immobilised to a solid surface or conjugated to a detectable marker for use in an immunoassay.

The invention further comprises an isolated nucleic acid molecule coding for a peptide comprising a C-terminal or N-terminal neo-epitope formed by cleavage of mimecan in any one of the partial sequences set out above.

The invention further comprises a vector comprising a nucleic acid sequence comprising an expression signal and a coding sequence which codes for the expression of a peptide comprising a C-terminal or N-terminal neo-epitope formed by cleavage of mimecan in any one of the partial sequences set out above and further includes a host cell transformed with such a vector and expressing a said peptide.

Yet another aspect of the invention relates to kits, which can be used conveniently for carrying out the methods described above.

Such kits may include (1) a microtitre plate coated with synthetic peptide carrying the sequence of the neo-epitope; (2) a monoclonal antibody or antibody binding fragment of the invention reactive with said synthetic peptide; and (3) a labelled anti-mouse IgG immunoglobulin. Alternatively, such kits may include (1) a microtitre plate coated with purified native protein fragments; (2) a monoclonal antibody recognising a neo-epitope on fragments of any one of said proteins, and reactive with said purified fragments; and (3) a labelled anti-mouse IgG immunoglobulin. Alternatively, such kits may include (1) a microtitre plate coated with streptavidin; (2) a synthetic peptide linked to biotin, said synthetic peptide carrying the sequence of a neo-epitope; (3) a monoclonal antibody recognising a neo-epitope on said protein fragments and reactive with said synthetic peptide; and (4) a labelled anti-mouse IgG immunoglobulin. Yet another alternative could be kits including (1) a microtitre plate coated with streptavidin; (2) a synthetic peptide linked to biotin, said peptide carrying the sequence of a neo-epitope; (3) a monoclonal antibody recognising a neo-epitope on said protein fragments (and reactive with said synthetic peptide) and conjugated to horseradish peroxidase. Yet another alternative could be a kit including (1) a microtitre plate coated (directly or indirectly) with a monoclonal antibody or a fragment thereof, said antibody recognising a neo-epitope on said protein fragment; (2) a HRP labelled synthetic peptide carrying the sequence of a neo-epitope. Or alternatively, a kit including (1) a microtitre plate coated (directly or indirectly) with a monoclonal antibody or a fragment thereof, said antibody recognising a neo-epitope on said protein fragment; (2) a biotin-labelled synthetic peptide carrying the sequence of a neo-epitope; (3) HRP-labelled streptavidin.

Thus, the invention includes an immunoassay kit comprising an immunological binding partner as described herein, and a competition agent which binds said immunological binding partner, and optionally one or more of a wash reagent, a buffer, a stopping reagent, an enzyme label, an enzyme label substrate, calibration standards, an anti-mouse antibody and instructions for conducting a said immunoassay.

The assays described herein are useful in the diagnosis of atherosclerotic disease in patients. In addition, the tests are useful for the assessment of disease progression, and the monitoring of response to therapy. The immunological binding partners of the invention may also be used in immunostaining to show the presence or location of cleavage products of any atherosclerotic plaque protein described herein.

The invention will be further explained and illustrated with reference to the accompanying drawings, in which.

FIGS. 3A-3C A and B show plasma levels of MMCN-151 in control (ctrl) and ApoE-KO mice, at baseline (BL), after 10 weeks and after 20 weeks of feeding either standard chow (FIG. 3A) or high fat diet (FIG. 3B) obtained in Example 1. In FIG. 3C control and ApoE-KO mice fed a normal diet are compared at 20 weeks.

Figure 4:
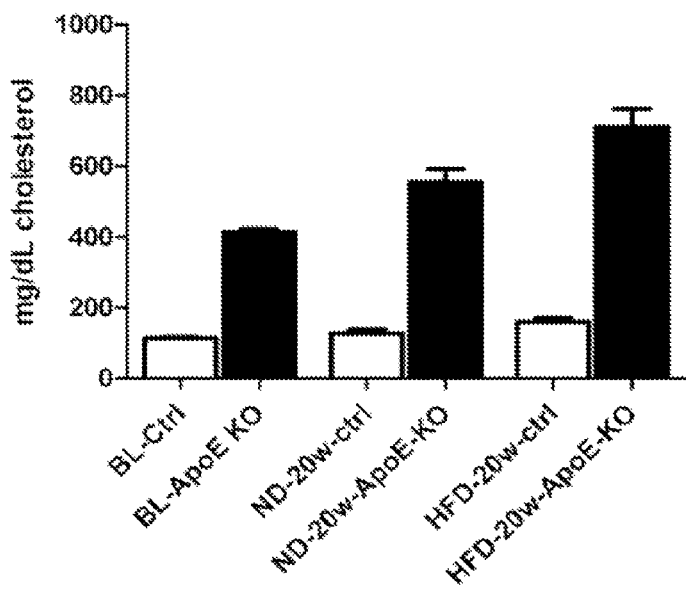

FIG. 4, results obtained in Example 1 showing the effect of diet on circulating levels of MMCN-151 neoepitope after 20 weeks of feeding. Here, we compare effect of normal diet (ND) with high-fat diet (HFD) in control (ctrl) and apolipoproteinE knockout (ApoE KO) mice plasma.

Figure 5A:
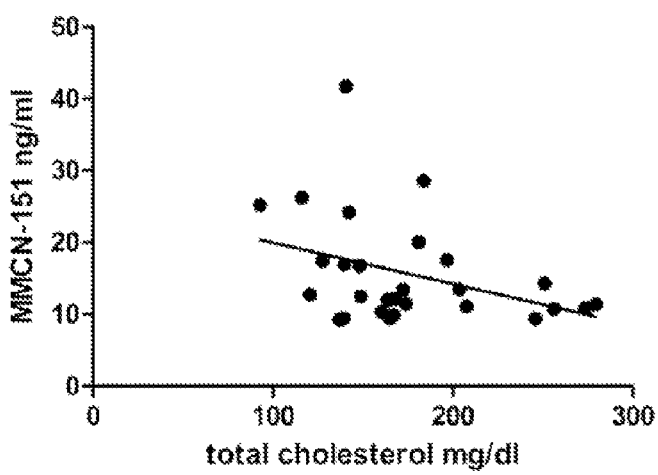
Figure 5B:
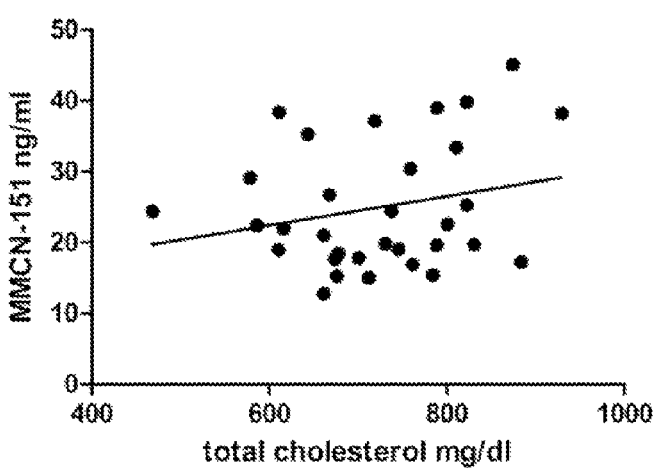

FIGS. 5A-5B show correlation between plasma cholesterol of control mice fed HFD and their plasma levels of mimecan fragments (FIG. 5A) and plasma cholesterol of ApoE KO mice fed HFD and the levels of mimecan fragments (FIG. 5B).

Figure 6:
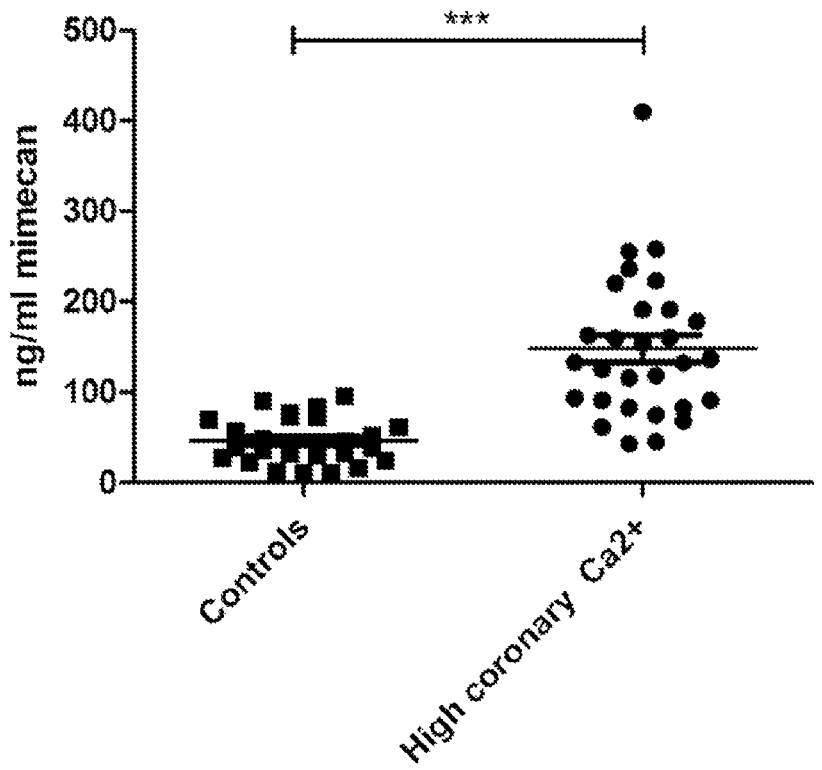

FIG. 6 shows plasma levels of mimecan fragments in human patients characterised by high $Ca^{2+}$ levels and controls.

Figure 7:
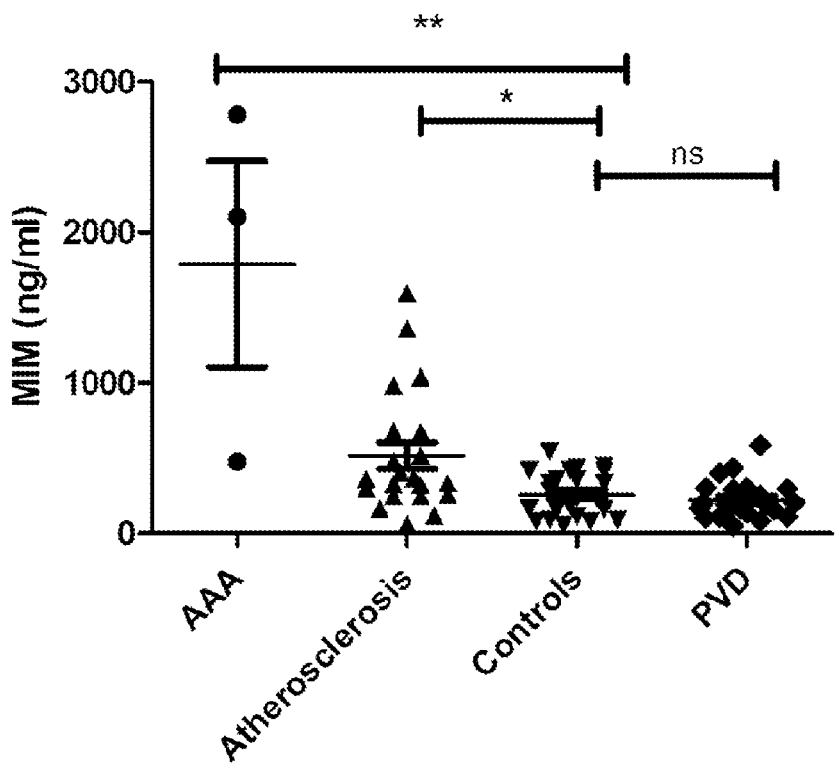

FIG. 7 shows results from a sandwich ELISA described below.

EXAMPLE 1

In Vitro Cleavage

Recombinant mouse mimecan (cat. No. 2949-MC-050, R&D Systems, DK) was cleaved with activated MMP-12 (cat.no.ab54058, Abcam, UK). To facilitate MMP-12 cleavage of mimecan, 1 mg/mL mimecan was filtered to remove proteins below 10.000 kDa (Microcon Ultracel YM-10, cat. no. 42407, Millipore, Billerica, Mass., USA). Protease cleavage was performed by mixing 100 μg mimecan and 1 μg of enzyme (MMP-12) in MMP buffer (100 mM Tris-HCl, 100 mM NaCl, 10 mM CaCl2, 2 mM Zn acetate, pH 8.0). As a control, 100 μg of mimecan was mixed with MMP buffer only. The mimecan cleavages were incubated for 24 hrs at 37° C. All cleavages were terminated using EDTA. Finally the cleavage was verified by visualization using the SilverXpress® Silver Staining Kit (cat. no. LC6100, Invitrogen, Carlsbad, Calif., USA) according to the manufacturer's instructions.

Peptide Identification

Peptide fragments in the in vitro cleaved samples were identified using matrix-assisted laser desorption time of flight mass spectrometry (MALDI-TOF MS) and liquid chromatography coupled to electro spray ionization (ESI) tandem mass spectrometry (LC-MS/MS). MALDI-TOF samples were purified using C18 zip-tips (cat.no.ZTC18SO24, Millipore, Billerica, Mass., USA) according to specifications and 0.1 μg of material was eluted onto a MTP 384 ground steel target plate (Bruker-Daltonics, Bremen, Germany). MALDI tandem mass spectra were recorded on a Bruker ultraflex MALDI-TOF/TOF mass spectrometer (Bruker-Daltonics, Bremen, Germany) in positive ion reflector mode. Mass spectra were externally calibrated in the m/z range of 800-4000 using peptides generated by tryptic digestion of bovine β-lactoglobulin. The m/z software "Flexanalysis" (Bruker-Daltonics, Bremen, Germany) was used to analyze spectra. LCMS samples were ultra-filtrated to remove proteins above 10 kDa, the pH was adjusted to 2.0 using formic acid, and a 4 μL sample was analyzed by LC-MS/MS. LC was performed on a nanoACQUITY UPLC BEH C18 column (Waters, Milford, Mass., USA) using a formic acid/acetonitrile gradient. MS and MS/MS were performed on a Synapt High Definition Mass Spectrometry quadruple time of flight MS (QUAD-TOF; Waters, Milford, Mass., USA), with acquisition range of 350-1600 m/z in MS and 50-2000 m/z, in MS/MS. The software "ProteinLynx Global SERVER (PLGS)" (Waters, Milford, Mass., USA) was used to analyze spectra and generate peak lists. To identify peptides, MS and MS/MS data was searched against mimecan (FASTA) protein database using the Mascot 2.2 (Matrix Science, Boston, Mass., USA) software with either the MALDI-TOF/TOF or ESI-QUAD-TOF settings.

EXAMPLE 2

Selection of Peptide for Immunizations

The first six amino acids of each free end of the sequences identified by MS were regarded as neo-epitopes generated by the protease in question. All obtained protease-generated sequences were analyzed for homology and distance to other cleavage sites and then blasted for homology using the NPS@: network protein sequence analysis.

Reagents and Peptides

All reagents were standard high-quality chemicals from companies such as Merck and Sigma Aldrich. The synthetic peptides used for monoclonal antibody production and validation were: (a) immunogenic peptide: Ovalbumin-GGC-EDIEDGTFSK (OVA)-SEQ ID NO 27, (b) screening peptide EDIEDGTFSK-SEQ ID NO 28, (c) de-selection peptide EDIEDGTFSKL-SEQ ID NO 29 which has been elongated with one amino acid in the C-terminus were purchased from Chinese Peptide Company, Beijing, China. Peptide conjugation reagents were produced by Pierce (Thermofisher, Denmark).

Buffers Used for the ELISAs

Buffer used for dissolving the coating peptide was composed of the following: 40 mM $NaHPO_4$, 12H20, 7 mM $KH_2PO_4$, 137 mM NaCl, 2.7 mM KCl, 25 mM EDTA, 0.1% TWEEN 20, a non-ionic detergent, 1% BSA, 10% sorbitol, pH 7.

Buffer containing following chemicals was used for incubation of serum/plasma assay: 100 mM TRIZMA, 0.05% TWEEN 20, 0.1% BSA, 0.36% Bronidox L5, pH 7.4. For washing steps, we used a buffer composed of: 25 mM TRIZMA, 50 mM NaCl, 0.036% Bronidox L5, 0.1% TWEEN 20, and reaction stopping buffer composed of 0.1% $H_2SO_4$.

ELISA-plates used for the assay development were Streptavidin-coated from Roche cat.: 11940279. All ELISA plates were analysed with the ELISA reader from Molecular Devices, SpectraMax M, (CA, USA).

Development of an ELISA

Methods for monoclonal antibody development are previously described (Barascuk et al. C3). Briefly, 4-6-week-old Balb/C mice were immunized subcutaneously with 200 µl emulsified antigen and 50 µg MMCN-151 (ED-IEDGTFSK) as Ovalbumin-GGC-EDIEDGTFSK. Consecutive immunizations were performed at 2-week intervals in Freund's incomplete adjuvant, until stable sera titre levels were reached, and the mice were bled from the 2nd immunization on. At each bleeding, the serum titre was detected and the mouse with highest antiserum titre was selected for fusion. The selected mouse was rested for 1 month followed by intravenous boosting with 50 µg MMCN-151 in 100 µl 0.9% Sodium Chloride solution 3 days before isolation of the spleen for cell fusion.

Fusion

The fusion procedure previously described[26] was followed with SP2/0 as myeloma cells. The fusion cells were cloned in 35-mm cell culture dishes by the semi-solid medium method and the dishes were incubated in a $CO_2$-incubator. Next, clones were plated into sixteen 96-well microtiter plates and left for three days, followed by screening of culture supernatants.

Antibody Screening

Supernatants were screened in a competitive ELISA setting. Peptide EDIEDGTFSK was used as the selection peptide and the EDIEDGTFSKL as the elongated peptide. Cell lines specific to selection peptide and without cross-reactivity to the elongated peptide were selected and the antibodies were purified.

MMCN-151 ELISA Methodology

In preliminary experiments, we optimized the reagents, their concentrations and the incubation periods by performing several checkerboard analyses. The MMCN-151 ELISA was developed as follows: A 96-well ELISA plate pre-coated with streptavidin was further coated with 1.25 ng/ml of the synthetic peptide Biotin-EDIEDGTFSK dissolved in PBS-TBE buffer at 20° C. for 30 min by constant shaking at 300 rpm. The plate was washed five times in washing buffer and 20 µl of sample was added, followed by 100 µl of peroxidase conjugated anti-human mAb-MMCN-151 solution (30 ng/ml). The plate was incubated for 1 h at 20° C. in 100 mM Tris-BT buffer during which time it was shaken at 300 rpm.

The plate was again washed five times followed by addition of 100 µl tetramethylbenzinidine (TMB) (Kem-En-Tec cat.4380H). The plate was incubated for 15 min in darkness and shaken at 300 rpm. In order to cease the reaction, 100 µl of stopping solution (95-97% H2SO4, Merck Cat. No.: 1.00731) was added and the plate was analysed in the ELISA reader at 450 nm with 650 nm as the reference.

Standards

A standard curve was performed by serial dilution of MMCN-151 (EDIEDGTFSK). Standard concentrations were 0, 0.3125, 6.25, 12.5, 25, 50, 100, 200 ng/ml.

Samples for Testing Native Reactivity of the Antibodies

During assay development and validation serum from healthy adult subjects of different age and gender were used. Serum samples are obtained from young healthy volunteers 23-50 years of age. The positive control used in the assays was the material obtained from in vitro cleavage of mimecan with purified human MMP-9 and MMP-12. We also tested serum samples from different species including mouse, rat, rabbit, monkey, pig to determine the level of interspecies cross reactivity.

Technical Evaluation of the ELISA

All ELISA's were developed according to the internal standard operating procedures. We addressed the following requirements:

Intra-assay precision and accuracy: 10 independent runs on 10 different plates have been performed on the test samples, which consisted of human serum.

Inter-assay precision and accuracy: This was determined by 10 independent assay runs of each validation sample on 10 different plates.

Lower Limit of Detection (LLD): In an analytical run, 40 determinations were made of the lowest standard (the zero standards). This was repeated three times. At each plate LLD was estimated as the following: LLD=mean-3×St.Dev. The LLD concentration was calculated using the 4-parametric-fit equation to generate the average LLD concentration.

Recovery: Four different samples covering more than 50% of the standard curve, from all dilutions, were back-calculated from diluted to undiluted to samples in order to estimate the recovery percentage.

Animal Samples

20 ApoE KO and 20 wild type C57 BL/6 male mice aged 10 weeks from Taconic, Europe A/S (Lille Skensved, Denmark) were fed either standard maintenance diet Altromin (product ID: 1320, Brogaarden, Denmark) or D12492 High fat diet containing 60% fat (Brogaarden, Denmark), ad libitum. Ethics guidelines for experimental investigations in animals were followed and the protocol was approved by the local Experimentation Ethics Committee—"Dyreforsogstilsynet". The study also conforms to the "Guide for care and use of laboratory animals published by US National Institute of Health. When mice were aged 10 (baseline), 20 and 30 weeks, plasma samples were collected by blood sampling using retro orbital puncture or, in the case of sacrifice, at weeks 20 or 30, by syringe aspiration from the jugular vein (around 1 ml). Heparinized (lithium heparin) blood was centrifuged, and plasma frozen at −20° C. until assayed. Plasma cholesterol was measured by enzymatic assays using an analyser from Molecular Devices, SpectraMax M, (CA, USA).

Densitometry

Densitometry measurements were performed using UN-SCAN-IT Version 6.1 from Silk Scientific, according to the manufacturer's guidelines.

Histology Image Analysis

Histology sections of mouse aorta were stained with Alcian blue and were analysed using Visiopharm software Version 3.2.8.0 (Hørsholm, Denmark). Visiopharm application allowed for quantification of specific tissue areas containing positive staining. Images were acquired using Pixelink PL-A623C microscope digital camera.

Statistical Analysis

For assay validation, optical density was fitted against analyte concentration applying a four-parameter logistic regression to the calibration curve. Average, standard deviations, percentage coefficient of variation (% CV), and differences from theoretical values were calculated for all standards and samples. Quantitative data were analysed using GraphPad Prism 5 (GraphPad Software, San Diego, Calif., USA). Significant differences between means were determined using the Student's two-tailed unpaired t-test, not assuming Gaussian distribution. Correlations between serum MMCN-151 values and the rest of the variables studied were analysed with Pearson's two-tailed test. Data was expressed as mean±standard error of the mean and differences were considered significant at a p level of 0.05 or lower.

Results

ELISA Technical Specifications

The antibody with best native reactivity, affinity and stability in the assay was chosen from the antibody-producing clones generated after the fusion of spleen- and myeloma cells. The clone chosen for antibody purification and the subsequent development of the ELISA was NB206-15B6-F8, raised against MMCN-151 antigen.

Standard Curve and Recovery

Figure 1:
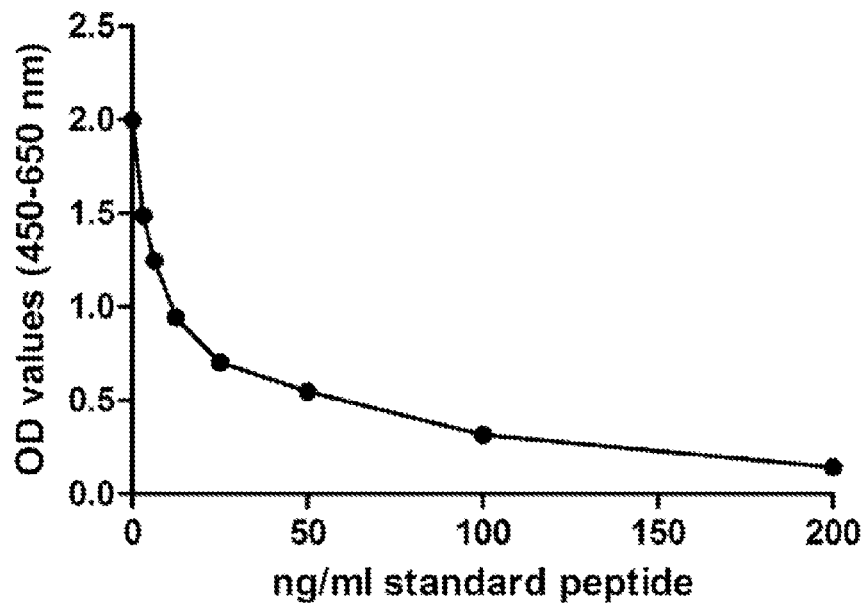
FIG. 1 shows and example of a 4-parametric fitted standard curve with peptide concentrations of 0, 3.125, 6.25, 12.5, 25, 50, 100 and 200 ng/ml obtained in Example 1.

A typical standard curve is presented in FIG. 1, showing chosen standards and the 4-parametric fit equation for determination of sample concentration, based on peptide concentrations of 0, 3.125, 6.25, 12.5, 25, 50, 100 and 200 ng/ml.

Determination of the linearity or recovery by dilution in different samples resulted in following. The average determined recoveries back-calculated from samples diluted 1:1, 1:2, 1:4, 1:8 and 1:16 to undiluted sample were close to 100% and within the recommended ±10% (data not shown).

Figure 2:
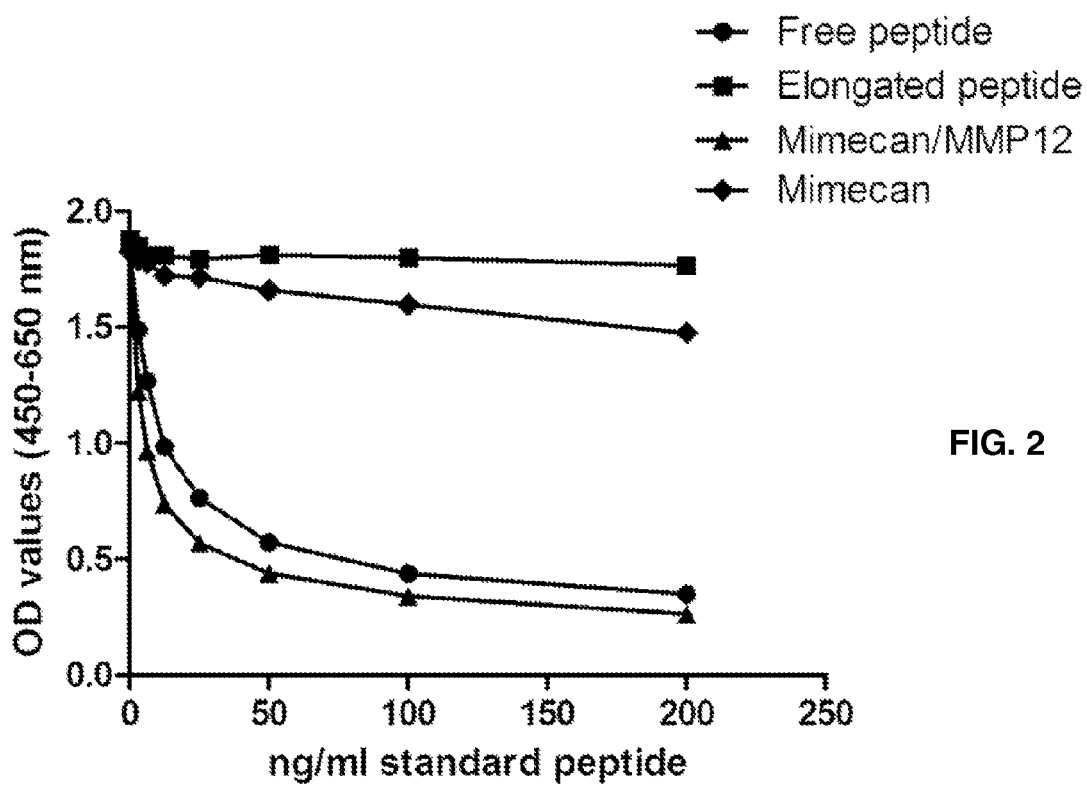
FIG. 2 shows competitive ELISA test results obtained in Example 1.

In order to ensure that the antibody produced is specific towards the neoepitope of mimecan and is not cross-reacting to either elongated peptide or whole mimecan, we tested the assay reactivity of MMP-12 cleaved mimecan compared to uncleaved mimecan and elongated peptide. FIG. 2 shows the results of the competitive ELISA test of MMCN-151 antibody reaction towards free peptide, elongated peptide, mimecan cleaved with MMP12 and intact mimecan. The x-axis is representative of the concentrations of free and elongated peptide. Concentrations of samples containing mimecan and mimecan cleaved with MMP12 are 43 ug/ml as the highest concentration followed by 2-fold dilutions of samples. As shown by FIG. 2, the MMCN-151 antibody is specific towards the synthetic free peptide(EDIEDGTFSK), resulting in the inhibition of signal from approximately 2.0 OD (450-650) to 0.5. Similar results are seen for in vitro cleaved mimecan by MMP12, where the signal inhibition follows the synthetic peptide curve. Moreover, there seems to be no inhibition of the signal in the sample containing the synthetic peptide elongated with one amino-acid EDIEDGTFSK<u>L</u>). Very weak competition is seen with intact mimecan at the highest concentration.

The lowest limit of detection (LLD) is defined as the lowest analyte concentration that can be quantitatively determined with suitable accuracy was 0.5 ng/ml in the assay.

Precision-Intra-Assay Variability and Inter-Assay Variability

Intra-assay variability, calculated as the average % coefficient of variation (% CV) from the readings of 10 replicates of four human serum samples and one rat serum sample. For the four human serum samples with an average concentration of MMCN-151 of 5 ng/ml, the average intra-assay variability was 1.3%. Rat serum sample had an average MMCN-151 concentration of 13 ng/ml with an average intra-assay variability of 1.1%.

Inter-assay mean % CVs were determined from the same sets of samples as the intra-assay and standards but on 10 different plates on 10 different days. The average inter-assay variability, between the highest and lowest levels detected, was 10.2%.

Plasma MMCN-151 Values Reflect Early Atherosclerosis in ApoE KO Mice.

Plasma MMCN-151 levels were measured in ApoE KO mice and in the C57bl6 controls at baseline, and at 10 and 20 weeks of feeding of either normal chow or high fat diet HFD, results are shown in FIGS. 3A-3B respectively. The effect of diet in ApoE KO mice was compared with ctrl mice at 20 weeks was compared in FIG. 3C.

The results of the one way ANOVA were significant (p<0.0001) both in control diet group and in HFD group; In particular, MMCN-151 values were significantly higher in ApoE-KO mice on HFD at both 10 and 20 weeks of feeding 12.1 ng/mL, p<0.001 and 18.2 ng/mL, p<0.001 respectively compared to the control mice on HFD with 5.7 ng/mL, p<0.001 and 10.4 ng/mL.

The effect of HFD on the levels of circulating MMCN-151 are significantly increased (p=0.002) in ApoE-KO mice compared to controls after 20 weeks of feeding. There was no effect on the levels of MMCN-151 in animals consuming control diet, see FIG. 3C.

Plasma Cholesterol Levels in Control and ApoE KO Mice.

FIG. 4 shows cholesterol levels measured in mice plasma at baseline and after 20 weeks of feeding normal diet (ND) or high fat diet (HFD) in either control mice (ctrl) or in ApoE-KO mice. A significantly higher level of cholesterol was identified in control mice when comparing baseline and 20 week time point for mice fed HFD (p<0.001), but not for mice fed ND. In the case of ApoE KO animals, there is as expected a significant increase in cholesterol after 20 weeks of feeding compared to baseline on both normal (p=0.001) and on HFD (p=0.001). Furthermore, there is a significant difference in cholesterol levels between ApoE KO and control mice at baseline and in both diet groups (p<0.001).

We also investigated the lineal relationship between plasma MMCN-151 values and total cholesterol in control mice after 20 weeks of HFD (r=0.48; p=0.276) ApoE-KO animals (r=0.04; p=0.931). FIGS. 5A-5B show linear correlation between plasma cholesterol of control mice fed HFD and their plasma levels of MMCN-151 and plasma cholesterol of ApoE KO mice fed HFD and the levels of MMCN-151, respectively.

Plasma MMCN-151 is Increased in Patients with Arterial Calcifications.

Further insight on the suitability of MMCN-151 as a surrogate indicator of pathological changes in the cardiovascular tissue was obtained by measuring plasma levels of MMCN-151 in patients diagnosed with high coronary calcium deposition in the cardiovascular system. We compared these plasma levels of MMCN-151 with plasma levels of age-matched controls with no diagnosed deposition of coronary calcium, FIG. 6.

The above work shows that there was significant increase in MMCN-151 in patients with coronary calcium depositions compared to their age-matched controls. Apart from the coronary calcium depositions, these two groups of patients seem similar, with no significant difference in plasma cholesterol levels, blood pressure or triglycerides.

In conclusion, we have developed technically robust competitive assay using a specific monoclonal antibody for the detection in human, rat and mouse serum and plasma of MMCN-151, a fragment of mimecan derived from MMP-9 and 12 degradation. We demonstrated that MMCN-151 was significantly elevated in ApoE KO mice fed high fat diet for 20 weeks in comparison with control mice. Additionally, we have shown that human plasma samples from patients diagnosed with extensive coronary calcium depositions was significantly elevated compared to age-matched controls. We have established the principle that neo-epitope containing fragments of mimecan provide valuable biomarkers for CVD and for atherosclerotic plaque calcification.

EXAMPLE 3

Sandwich ELISA Assay

A sandwich ELISA assay for mimecan has been developed as follows: a catcher antibody is directed towards the neo-epitope sequence $\mathrm{EDIEDGTFSK}^{\downarrow'165}$ generated by in vitro cleavage of mimecan by MMP9 and MMP12 and a tracer HRP-labelled antibody is directed towards the partially overlapping sequence $^{151}$'TGNLIEDIED'$^{160}$. The ELISA procedure was as follows: a 96-well streptavidin pre-coated plate is coated with 1 μg/mL of the biotinylated catcher antibody, dissolved in 25 mM PBS-BTB buffer and incubated for 1 hour at 20° C. Calibrators were prepared by 2-fold dilution of a human serum sample with elevated concentration of the antigens (MIM2, mimecan fragments). 20 μL of the calibrator or sample were added to appropriate wells, followed by 100 μL of 25 mM PBS-BTB buffer and incubation for 1 hour at 20° C. 100 μl of 1 μg/ml HRP-conjugated tracer antibody was added to the well and incubated for 1 hour at 20° C. Finally, 100 μL tetramethyl benzidine (TMB) (Kem-En-Tec cat.438OH, Taastrup, Denmark) developer was added, and the plate was incubated for 15 minutes at 20° C. in the dark. All the above incubation steps included shaking at 300 rpm. After each incubation step the plate was washed five times in washing buffer (20 mM Tris, 50 mM NaCl, pH 7.2). The TMB reaction was stopped by adding 100 μL of stopping solution (1% HCl) and measured at 450 nm with 650 nm as the reference. A standard calibration curve was plotted using a 4-parametric mathematical fit model with a starting concentration of 500 ng/mL for the calibrator following a 2-fold dilution and the last standard was a zero standard.

This assay was used to measure CVD plasma samples obtained through an academic collaboration. The group of patients included abdominal aortic aneurism patients (AAA) (n=6, 3f, 3m, average age=69,16±18,36, average BMI=27±4,33), atherosclerosis patients (n=40, 13f, 27m, average age=69,25±10,18, BMI=27,63±7,17), peripheral vascular disease patients (PVD) (n=22, 8f, 14m, average age=68,33±9,94, BMI=30,84±5,00) and control patients formed by surgical patients not affected by CVD (n=25, 14f, 11m, average age=54,57±18,46, BMI=31,19±7,9).

The results are shown in FIG. 7. The data show a significantly higher presence of the investigated mimecan fragment (MIM2) in plasma of patients with abdominal aortic aneurism (AAA). Three of the plasma samples from patients with AAA had MIM2 values far above the measuring range and were therefore not included in the figure. In addition, plasma samples from atherosclerotic patients were elevated compared to controls. No difference was observed in peripheral vascular disease (PVD) patients compared to controls. These data show the potential of this mimecan fragment assessed in a sandwich assay as a non-invasive marker of cardiovascular diseases and indicate that mimecan remodeling is an important event in the pathogenesis of CVD, leading to the release of mimecan fragments into circulation.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference.

REFERENCE LIST

American Heart Association. Heart *Disease and Stroke Statistics—2007 Update*. Dallas, Tex.: American Heart Association; 2007. http://www americanheart.org/downloadable/heart/1166712318459HS_StatsInsid eText pdf 2007.

Arroyo L H, Lee R T. Mechanisms of plaque rupture: mechanical and biologic interactions. *Cardiovasc Res* 1999 February; 41(2):369-75.

Barascuk N, Veidal S S, Larsen L et al. A novel assay for extracellular matrix remodeling associated with liver fibrosis: An enzyme-linked immunosorbent assay (ELISA) for a MMP-9 proteolytically revealed neo-epitope of type III collagen. *Clin Biochem* Apr. 7, 2010.

Bellosta S, Baetta R, Canavesi M et al. Raloxifene inhibits matrix metalloproteinases expression and activity in macrophages and smooth muscle cells. *Pharmacol Res* 2007 August; 56(2):160-7.

Bobryshev Y V. Calcification of elastic fibers in human atherosclerotic plaque. Atherosclerosis 2005; 180:293-303.

Brown, D. C. and K. G. Vogel. "Characteristics of the in vitro interaction of a small proteoglycan (PG II) of bovine tendon with type I collagen." Matrix. 9.6 (1989): 468-78.

Cattin L, Fisicaro M, Tonizzo M, Valenti M, Danek G M, Fonda M, Da Col P G, Casagrande S, Pincetri E, Bovenzi M, and Baralle F. Polymorphism of the apolipoprotein E gene and early carotid atherosclerosis defined by ultrasonography in asymptomatic adults. Arterioscler Thromb Vasc Biol. 1997 January; 17(1):91-4.

Chapman H A, Riese R J, Shi G P. Emerging roles for cysteine proteases in human biology. Annu. Rev. Physiol 1997; 59:63-88.

Clarkson T B, Kaplan J R. Stage of Reproductive Life, Atherosclerosis Progression and Estrogen Effects on Coronary Artery Atherosclerosis, In: Lobo R A, editor. Treatment of the Postmenopausal Woman: Basic and Clinical Aspects, 3 ed. San Diego: Elsevier; 2007. p. 509-28.

Death A K, Fisher E J, McGrath K C, Yue D K. High glucose alters matrix metalloproteinase expression in two key vascular cells: potential impact on atherosclerosis in diabetes. *Atherosclerosis* 2003 June; 168(2):263-9.

Danielson, K. G., et al. "Targeted disruption of decorin leads to abnormal collagen fibril morphology and skin fragility." J. Cell Biol. 136.3 (1997): 729-43. Dours-Zimmermann, M. T. and D. R. Zimmermann. "A novel glycosaminoglycan attachment domain identified in two alternative splice variants of human versican." J. Biol. Chem. 269.52 (1994): 32992-98.

Eriksen H A, Satta J, Risteli J, Veijola M, Vare P, Soini Y. Type I and type III collagen synthesis and composition in the valve matrix in aortic valve stenosis. Atherosclerosis 2006; 189:91-98.

Evanko, S. P., et al. "Proteoglycan distribution in lesions of atherosclerosis depends on lesion severity, structural characteristics, and the proximity of platelet-derived growth factor and transforming growth factor-beta." Am. J. Pathol. 152.2 (1998): 533-46.

Funderburgh, J. L. "Keratan sulfate: structure, biosynthesis, and function." Glycobiology 10.10 (2000): 951-58.

Funderburgh, J. L., et al. "Macrophage receptors for lumican. A corneal keratan sulfate proteoglycan." Invest Ophthalmol. Vis. Sci. 38.6 (1997): 1159-67.

Funderburgh J L, Corpuz L M, Roth M R, Funderburgh M L, Tasheva E S, Conrad G W. Mimecan, the 25-kDa corneal keratan sulfate proteoglycan, is a product of the gene producing osteoglycin. *J Biol Chem* Oct. 31, 1997; 272(44):28089-95.

Gabay C and Kushner I. Acute-phase proteins and other systemic responses to inflammation. N Engl J Med. Feb. 11, 1999; 340(6):448-54.

Garcia-Touchard A, Henry T D, Sangiorgi G et al. Extracellular proteases in atherosclerosis and restenosis. *Arterioscler Thromb Vasc Biol* 2005 June; 25(6):1119-27.

Gardner C D, Fortmann S P, Krauss R M. Association of small low-density lipoprotein particles with the incidence of coronary artery disease in men and women. JAMA 1996; 276:875-81.

Garrone R, Lethias C, Le Guellec D. Distribution of minor collagens during skin development. Microsc. Res Tech. 1997; 38:407-12.

Gefter M L, Margulies D H, Scharff M D. A simple method for polyethylene glycol-promoted hybridization of mouse myeloma cells. Somatic Cell Genet 1977 March; 3(2): 231-6.

Graham I, Atar D, Borch-Johnsen K, Boysen G, Burell G, Cifkova R et al. European guidelines on cardiovascular disease prevention in clinical practice: executive summary. Atherosclerosis 2007; 194:1-45.

Halpert I, Sires U I, Roby J D et al. Matrilysin is expressed by lipid-laden macrophages at sites of potential rupture in atherosclerotic lesions and localizes to areas of versican deposition, a proteoglycan substrate for the enzyme. Proc Natl Acad Sci USA Sep. 3, 1996; 93(18):9748-53.

Haraki T, Takegoshi T, Kitoh C, Wakasugi T, Saga T, Hirai J I, Aoyama T, Inazu A and Mabuchi H, Carotid artery intima-media thickness and brachial artery flow-mediated vasodilation in asymptomatic Japanese male subjects amongst apolipoprotein E phenotypes. J Intern Med. 2002 August; 252(2):114-20.

Hatanaka K, Li X A, Masuda K, Yutani C and Yamamoto A, Immunohistochemical localization of C-reactive protein-binding sites in human atherosclerotic aortic lesions by a modified streptavidin-biotin-staining method. Pathol Int. 1995 September; 45(9):635-41.

Heegaard A M, Corsi A, Danielsen C C, Nielsen K L, Jorgensen H L, Riminucci M, Young M F and Bianco P, Biglycan deficiency causes spontaneous aortic dissection and rupture in mice. Circulation. May 29, 2007; 115(21): 2731-8. Epub May 14, 2007.

Herman M P, Sukhova G K, Libby P, Gerdes N, Tang N, Horton D B et al. Expression of neutrophil collagenase (matrix metalloproteinase-8) in human atheroma: a novel collagenolytic pathway suggested by transcriptional profiling. Circulation 2001; 104:1899-904.

Host N B, Jensen L T, Bendixen P M, Jensen S E, Koldkjaer O G, Simonsen E E. The aminoterminal propeptide of type III procollagen provides new information on prognosis after acute myocardial infarction. *Am J Cardiol* Nov. 1, 1995; 76(12):869-73.

Jeppesen J, Hein H O, Suadicani P, Gyntelberg F. High triglycerides/low high-density lipoprotein cholesterol, ischemic electrocardiogram changes, and risk of ischemic heart disease. Am Heart J 2003; 145:103-08.

Johnson J L. Matrix metalloproteinases: influence on smooth muscle cells and atherosclerotic plaque stability. *Expert Rev Cardiovasc Ther* 2007 March; 5(2):265-82.

Kampmann A, Fernandez B, Deindl E et al. The proteoglycan osteoglycin/mimecan is correlated with arteriogenesis. *Mol Cell Biochem* 2009 February; 322(1-2):15-23.

Karsdal M A, Henriksen K, Leeming D J et al. Biochemical markers and the FDA Critical Path: how biomarkers may contribute to the understanding of pathophysiology and provide unique and necessary tools for drug development. *Biomarkers* May 2009; 14(3):181-202.

Karsdal M A, Byrjalsen I, Leeming D J, Christiansen C. Tibolone inhibits bone resorption without secondary positive effects on cartilage degradation. *BMC Musculoskelet Disord* 2008; 9:153.

Katsuda S, Kaji T. Atherosclerosis and extracellular matrix. J Atheroscler Thromb 2003; 10(5):267-74.

Knox, S. M. and J. M. Whitelock. "Perlecan: how does one molecule do so many things?" Cell Mol. Life Sci. 63.21 (2006): 2435-45.

Koenig W, Khuseyinova N. Biomarkers of atherosclerotic plaque instability and rupture. *Arterioscler Thromb Vasc Biol* 2007; January; 27(1):15-26.

Kragel A H, Reddy S G, Wittes J T, Roberts W C. Morphometric analysis of the composition of atherosclerotic plaques in the four major epicardial coronary arteries in acute myocardial infarction and in sudden coronary death. *Circulation* 1989 December; 80(6):1747-56.

Kuller L H, Tracy R P, Shaten J and Meilahn E N, Relation of C-reactive protein and coronary heart disease in the MRFIT nested case-control study. Multiple Risk Factor Intervention Trial. Am J Epidemiol. Sep. 15, 1996; 144 (6):537-47.

Kunz J. Matrix metalloproteinases and atherogenesis in dependence of age. Gerontology. 2007; 53:63-73.

Kuzuya M, Nakamura K, Sasaki T, Cheng X W, Itohara S, Iguchi A. Effect of MMP-2 deficiency on atherosclerotic lesion formation in apoE-deficient mice. Arterioscler. Thromb. Vasc. Biol 2006; 26:1120-25.

Lauer-Fields J L, Juska D, Fields G B. Matrix metalloproteinases and collagen catabolism. *Biopolymers* 2002; 66(1):19-32.

Lawrie T D, Mcalpine S G, Rifkind B M, Robinson J F. Serum fatty-acid patterns in coronary-artery disease. Lancet 1961; 1:421-24.

Leinonen M and Saikku P, Evidence for infectious agents in cardiovascular disease and atherosclerosis. Lancet Infect Dis. 2002 January; 2(1):11-7.

Liu J, Sukhova G K, Sun J S, Xu W H, Libby P, Shi G P. Lysosomal cysteine proteases in atherosclerosis. Arterioscler. Thromb. Vasc. Biol 2004; 24:1359-66.

Lutgens, S. P., et al. "Cathepsin cysteine proteases in cardiovascular disease." FASEB J. 21.12 (2007): 3029-41.

Luttun A, Lutgens E, Manderveld A et al. Loss of matrix metalloproteinase-9 or matrix metalloproteinase-12 protects apolipoprotein E-deficient mice against atherosclerotic media destruction but differentially affects plaque growth. *Circulation* Mar. 23, 2004; 109(11):1408-14.

Mayne R. Collagenous proteins of blood vessels. Arteriosclerosis. 1986; 6:585-93.

McCullagh K G, Duance V C, Bishop K A. The distribution of collagen types I, III and V (AB) in normal and atherosclerotic human aorta. *J Pathol* 1980 January; 130(1):45-55.

Mecham R P, Broekelmann T J, Fliszar C J, Shapiro S D, Welgus H G, Senior R M. Elastin degradation by matrix metalloproteinases. Cleavage site specificity and mechanisms of elastolysis. *J Biol Chem* Jul. 18, 1997; 272(29):18071-6.

Mendall M A, Patel P, Ballam L, Strachan D and Northfield T C. C reactive protein and its relation to cardiovascular risk factors: a population based cross sectional study., BMJ. Apr. 27, 1996; 312(7038):1061-5.

Monfort J, Nacher M, Montell E, Vila J, Verges J and Benito P, Chondroitin sulfate and hyaluronic acid (500-730 kda) inhibit stromelysin-1 synthesis in human osteoarthritic chondrocytes. Drugs Exp Clin Res. 2005; 31(2):71-6.

Moreno P R, Falk E, Palacios I F, Newell J B, Fuster V, Fallon J T. Macrophage infiltration in acute coronary syndromes. Implications for plaque rupture. *Circulation* 1994 August; 90(2):775-8.

Pasceri V, Willerson J T and Yeh E T, Direct proinflammatory effect of C-reactive protein on human endothelial cells. Circulation. Oct. 31, 2000; 102(18):2165-8.

Register T C, Cann J A, Kaplan J R, Williams J K, Adams M R, Morgan T M et al. Effects of soy isoflavones and conjugated equine estrogens on inflammatory markers in atherosclerotic, ovariectomized monkeys. J Clin Endocrinol Metab 2005; 90:1734-40.

Reynolds G D and Vance R P. C-reactive protein immunohistochemical localization in normal and atherosclerotic human aortas. Arch Pathol Lab Med. 1987 March; 111(3):265-9.

Ridker P M, Intrinsic fibrinolytic capacity and systemic inflammation: novel risk factors for arterial thrombotic disease. Haemostasis. 1997; 27 Suppl 1:2-11.

Ridker P M, Hennekens C H, Buring J E and Rifai N. C-reactive protein and other markers of inflammation in the prediction of cardiovascular disease in women. N Engl J Med. Mar. 23, 2000; 342(12):836-43.

Rodriguez-Lee M, Bondjers G and Camejo G, Fatty acid-induced atherogenic changes in extracellular matrix proteoglycans. Curr Opin Lipidol. 2007 October; 18(5):546-53

Rosenquist C, Fledelius C, Christgau S et al. Serum Cross-Laps One Step ELISA. First application of monoclonal antibodies for measurement in serum of bone-related degradation products from C-terminal telopeptides of type I collagen. *Clin Chem* 1998 November; 44(11):2281-9.

Rouis M. Matrix metalloproteinases: a potential therapeutic target in atherosclerosis. Curr Drug Targets. Cardiovasc Haematol Disord. 2005; 5:541-48.

Rudel L L, Haines J, Sawyer J K, Shah R, Wilson M S, Carr T P. Hepatic origin of cholesteryl oleate in coronary artery atherosclerosis in African green monkeys. Enrichment by dietary monounsaturated fat. J Clin Invest 1997; 100:74-83.

Salisbury B G and Wagner, W D J Biol Chem. Aug. 10, 1981; 256(15):8050-7, 'Isolation and preliminary characterization of proteoglycans dissociatively extracted from human aorta'.

Satta J, Juvonen T, Haukipuro K, Juvonen M, Kairaluoma M I. Increased turnover of collagen in abdominal aortic aneurysms, demonstrated by measuring the concentration of the aminoterminal propeptide of type III procollagen in peripheral and aortal blood samples. J Vasc. Surg. 1995; 22:155-60.

Schaar J A, Mastik F, Regar E, den Uil C A, Gijsen F J, Wentzel J J et al. Current diagnostic modalities for vulnerable plaque detection. Curr Pharm Des. 2007; 13:995-1001.

Shanahan C M, Cary N R, Osbourn J K, Weissberg P L. Identification of osteoglycin as a component of the vascular matrix. Differential expression by vascular smooth muscle cells during neointima formation and in atherosclerotic plaques. *Arterioscler Thromb Vasc Biol* 1997 November; 17(11):2437-47.

Shekhonin B V, Domogatsky S P, Muzykantov V R, Idelson G L, Rukosuev V S. Distribution of type I, III, IV and V collagen in normal and atherosclerotic human arterial wall: immunomorphological characteristics. *Coll Relat Res* 1985 September; 5(4):355-68.

Siest G, Pillot T, Regis-Bailly A, Leininger-Muller B, Steinmetz J, Galteau M M and Visvikis S, Apolipoprotein E: an important gene and protein to follow in laboratory medicine. Clin Chem. 1995 August; 41(8 Pt 1):1068-86.

Shin, J., J. E. Edelberg, and M. K. Hong. "Vulnerable atherosclerotic plaque: clinical implications." Curr. Vasc. Pharmacol. 1.2 (2003): 183-204.

Sondergaard B C, Wulf H, Henriksen K et al. Calcitonin directly attenuates collagen type II degradation by inhibition of matrix metalloproteinase expression and activity in articular chondrocytes. *Osteoarthritis Cartilage* 2006 August; 14(8):759-68.

Stary H C. Composition and classification of human atherosclerotic lesions. Virchows Arch A. Pathol Anat. Histopathol. 1992; 421:277-90.

Sundstrom J, Vasan R S. Circulating biomarkers of extracellular matrix remodeling and risk of atherosclerotic events. Curr Opin Lipidol. 2006; 17:45-53.

Talusan, P., et al. "Analysis of intimal proteoglycans in atherosclerosis-prone and atherosclerosis-resistant human arteries by mass spectrometry." Mol. Cell Proteomics. 4.9 (2005): 1350-57.

Tasheva E S, Corpuz L M, Funderburgh J L, Conrad G W. Differential splicing and alternative polyadenylation generate multiple mimecan mRNA transcripts. *J Biol Chem* Dec. 19, 1997; 272(51):32551-6.

Thompson D, Banks R E, Forbes M A, Storr M, Higginson J, Raynes J, Illingworth J M, Perren T J, Selby P J and Whicher J T, The acute phase protein response in patients receiving subcutaneous IL-6. Clin Exp Immunol. 1995 October; 102(1):217-23.

Terry J G, Howard G, Mercuri M, Bond M G and Crouse J R 3rd. Apolipoprotein E polymorphism is associated with segment-specific extracranial carotid artery intima-media thickening, Stroke. 1996 October; 27(10):1755-9.

Tracy R P, Lemaitre R N, Psaty B M, Ives D G, Evans R W, Cushman M, Meilahn E N and Kuller L H, Relationship of C-reactive protein to risk of cardiovascular disease in the elderly. Results from the Cardiovascular Health Study and the Rural Health Promotion Project. Arterioscler Thromb Vasc Biol. 1997 June; 17(6):1121-7.

Turu M M, Krupinski J, Catena E, Rosell A, Montaner J, Rubio F et al. Intraplaque MMP-8 levels are increased in asymptomatic patients with carotid plaque progression on ultrasound. Atherosclerosis 2006; 187:161-69.

Uemura S, Matsushita M, Li W et al. Diabetes mellitus enhances vascular matrix metalloproteinase activity: role of oxidative stress. *Circ Res* Jun. 22, 2001; 88(12):1291-8.

Veidal S S, Bay-Jensen A C, Tougas G, Karsdal M A, Vainer B. Serum markers of liver fibrosis: combining the BIPED classification and the neo-epitope approach in the development of new biomarkers. *Dis Markers* 2010; 28(1):15-28.

Venugopal S K, Devaraj S, Yuhanna I, Shaul P and Jialal I. Demonstration that C-reactive protein decreases eNOS expression and bioactivity in human aortic endothelial cells, Circulation. Sep. 17, 2002; 106(12):1439-41.

Wagner W D. Proteoglycan structure and function as related to atherosclerosis. *Ann N Y Acad Sci* 1985; 454:52-68.: 52-68.

Wang T J, Gona P, Larson M G, Tofler G H, Levy D, Newton-Cheh C et al. Multiple biomarkers for the prediction of first major cardiovascular events and death. N Engl J Med 2006; 355:2631-39.

Whitelock, J. M. and R. V. Iozzo. "Heparan sulfate: a complex polymer charged with biological activity." Chem. Rev. 105.7 (2005): 2745-64.

Wight, T. N. "The extracellular matrix and atherosclerosis." Curr. Opin. Lipidol. 6.5 (1995): 326-34.

Wight, T. N., et al. "Vascular cell proteoglycans: evidence for metabolic modulation." Ciba Found. Symp. 124 (1986): 241-59.

Wight T N, Versican: a versatile extracellular matrix proteoglycan in cell biology. Curr Opin Cell Biol. 2002 October; 14(5):617-23.

Wight T N and Merrilees M J, Proteoglycans in atherosclerosis and restenosis: key roles for versican. Circ Res. May 14, 2004; 94(9):1158-67.

Wilson P W, Schaefer E J, Larson M G and Ordovas J M. Apolipoprotein E alleles and risk of coronary disease. A meta-analysis. Arterioscler Thromb Vasc Biol. 1996 October; 16(10):1250-5.

Yamada Y, Izawa H, Ichihara S, Takatsu F, Ishihara H, Hirayama H et al. Prediction of the risk of myocardial infarction from polymorphisms in candidate genes. N Engl J Med 2002; 347:1916-23.

Yamada S, Wang K Y, Tanimoto A et al. Matrix metalloproteinase 12 accelerates the initiation of atherosclerosis and stimulates the progression of fatty streaks to fibrous plaques in transgenic rabbits. *Am J Pathol* May 2008; 172(5):1419-29.

Zwaka T P, Hombach V and Torzewski J. C-reactive protein-mediated low density lipoprotein uptake by macrophages: implications for atherosclerosis., Circulation. Mar. 6, 2001; 103(9):1194-7.

The invention claimed is:

1. A method of detecting peptide fragments comprising an N- or C-terminal neo-epitope formed by cleavage in vivo of mimecan by a proteinase in a patient, said method comprising:
   a. obtaining a biofluid sample from a human patient; and
   b. detecting whether said peptide fragments of mimecan are present in the biofluid sample by contacting the biofluid sample with an antibody and detecting binding between the fragments and the antibody;
   wherein said antibody is raised against a synthetic peptide corresponding to a C-terminal or N-terminal neo-epitope amino acid sequence formed by cleavage of mimecan by a proteinase and has specific binding affinity for said C-terminal or N-terminal neo-epitope amino acid sequence, and wherein said antibody has specific binding affinity for any of the following sequences at the N terminal of a peptide:

| | |
|---|---|
| DFADIP | SEQ ID NO: 13 |
| TGNLIE | SEQ ID NO: 14 |
| LDFTGN | SEQ ID NO: 15 |
| RLDFTG | SEQ ID NO: 16 |
| RLEGNP | SEQ ID NO: 17 |
| DFTGNL | SEQ ID NO: 18 |
| DHNALE | SEQ ID NO: 19 |
| DIDAVP | SEQ ID NO: 20 |
| FTGNLI | SEQ ID NO: 21; |
| GNLIED | SEQ ID NO: 22 | or wherein said antibody has specific binding affinity for any of the following sequences at the C terminal of a peptide

| | |
|---|---|
| DIPNLR | SEQ ID NO: 23 |
| DGTFSK | SEQ ID NO: 24 |
| PIVLGK | SEQ ID NO: 25 |
| DIEDGT | SEQ ID NO: 26. |

2. A method as claimed in claim 1, wherein said antibody has specific binding affinity for the sequence EDIEDGTFSK (SEQ ID NO: 28) at the C terminal of a peptide or has specific binding affinity for the sequence TGNLIEDIED (SEQ ID NO: 30) at the N terminal of a peptide.

3. A method as claimed claim 1, wherein said antibody is a monoclonal antibody or a fragment of a monoclonal antibody having specific binding affinity.

4. A method as claimed in claim 1, wherein said method is conducted as a competition immunoassay in which said antibody and a competition agent are incubated in the presence of said sample and the competition agent competes with the peptide fragments in the sample to bind to the antibody.

5. A method as claimed in claim 4, wherein said competition agent is a synthetic peptide or is a purified native peptide formed by cleavage of the protein from which said epitope comes so as to reveal said neo-epitope.

6. A method as claimed in claim 1, wherein said method is conducted as a sandwich immunoassay in which said antibody and a further antibody having specific binding affinity for a peptide sequence contained in peptide fragments bound by said antibody are incubated in the presence of said sample and both bind together to said peptide fragments in the sample.

7. A method as claimed in claim 1, wherein the sample is a sample of urine, serum, blood, plasma, or saliva.

* * * * *

SEQUENCE LISTING

```
<160> NUMBER OF SEQ ID NOS: 30

<210> SEQ ID NO 1
<211> LENGTH: 9
<212> TYPE: PRT
<213> ORGANISM: Artificial sequence
<220> FEATURE:
<221> NAME/KEY: PEPTIDE
<222> LOCATION: 138..146
<223> OTHER INFORMATION: Mimecan cleavage peptide

<400> SEQUENCE: 1

Asp Phe Ala Asp Ile Pro Asn Leu Arg
1               5

<210> SEQ ID NO 2
<211> LENGTH: 15
<212> TYPE: PRT
<213> ORGANISM: Artificial sequence
<220> FEATURE:
<221> NAME/KEY: PEPTIDE
<222> LOCATION: 151..165
<223> OTHER INFORMATION: Mimecan cleavage peptide

<400> SEQUENCE: 2

Thr Gly Asn Leu Ile Glu Asp Ile Glu Asp Gly Thr Phe Ser Lys
1               5                   10                  15

<210> SEQ ID NO 3
<211> LENGTH: 18
<212> TYPE: PRT
```

```
<213> ORGANISM: Artificial sequence
<220> FEATURE:
<221> NAME/KEY: PEPTIDE
<222> LOCATION: 148..165
<223> OTHER INFORMATION: Mimecan cleavage peptide

<400> SEQUENCE: 3

Leu Asp Phe Thr Gly Asn Leu Ile Glu Asp Ile Glu Asp Gly Thr Phe
1               5                   10                  15
Ser Lys

<210> SEQ ID NO 4
<211> LENGTH: 10
<212> TYPE: PRT
<213> ORGANISM: Artificial sequence
<220> FEATURE:
<221> NAME/KEY: PEPTIDE
<222> LOCATION: 272..281
<223> OTHER INFORMATION: Mimecan cleavage peptide

<400> SEQUENCE: 4

Leu Glu Gly Asn Pro Ile Val Leu Gly Lys
1               5                   10

<210> SEQ ID NO 5
<211> LENGTH: 16
<212> TYPE: PRT
<213> ORGANISM: Artificial sequence
<220> FEATURE:
<221> NAME/KEY: PEPTIDE
<222> LOCATION: 147..162
<223> OTHER INFORMATION: Mimecan cleavage peptide

<400> SEQUENCE: 5

Arg Leu Asp Phe Thr Gly Asn Leu Ile Glu Asp Ile Glu Asp Gly Thr
1               5                   10                  15

<210> SEQ ID NO 6
<211> LENGTH: 19
<212> TYPE: PRT
<213> ORGANISM: Artificial sequence
<220> FEATURE:
<221> NAME/KEY: PEPTIDE
<222> LOCATION: 147..165
<223> OTHER INFORMATION: Mimecan cleavage peptide

<400> SEQUENCE: 6

Arg Leu Asp Phe Thr Gly Asn Leu Ile Glu Asp Ile Glu Asp Gly Thr
1               5                   10                  15
Phe Ser Lys

<210> SEQ ID NO 7
<211> LENGTH: 11
<212> TYPE: PRT
<213> ORGANISM: Artificial sequence
<220> FEATURE:
<221> NAME/KEY: PEPTIDE
<222> LOCATION: 271..281
<223> OTHER INFORMATION: Mimecan cleavage peptide

<400> SEQUENCE: 7

Arg Leu Glu Gly Asn Pro Ile Val Leu Gly Lys
1               5                   10

<210> SEQ ID NO 8
<211> LENGTH: 17
<212> TYPE: PRT
```

```
<213> ORGANISM: Artificial sequence
<220> FEATURE:
<221> NAME/KEY: PEPTIDE
<222> LOCATION: 149..165
<223> OTHER INFORMATION: Mimecan cleavage peptide

<400> SEQUENCE: 8

Asp Phe Thr Gly Asn Leu Ile Glu Asp Ile Glu Asp Gly Thr Phe Ser
1               5                   10                  15
Lys

<210> SEQ ID NO 9
<211> LENGTH: 17
<212> TYPE: PRT
<213> ORGANISM: Artificial sequence
<220> FEATURE:
<221> NAME/KEY: PEPTIDE
<222> LOCATION: 221..237
<223> OTHER INFORMATION: Mimecan cleavage peptide

<400> SEQUENCE: 9

Asp His Asn Ala Leu Glu Ser Val Pro Leu Asn Leu Pro Glu Ser Leu
1               5                   10                  15
Arg

<210> SEQ ID NO 10
<211> LENGTH: 10
<212> TYPE: PRT
<213> ORGANISM: Artificial sequence
<220> FEATURE:
<221> NAME/KEY: PEPTIDE
<222> LOCATION: 110..119
<223> OTHER INFORMATION: Mimecan cleavage peptide

<400> SEQUENCE: 10

Asp Ile Asp Ala Val Pro Pro Leu Pro Lys
1               5                   10

<210> SEQ ID NO 11
<211> LENGTH: 10
<212> TYPE: PRT
<213> ORGANISM: Artificial sequence
<220> FEATURE:
<221> NAME/KEY: PEPTIDE
<222> LOCATION: 150..165
<223> OTHER INFORMATION: Mimecan cleavage peptide

<400> SEQUENCE: 11

Asp Ile Asp Ala Val Pro Pro Leu Pro Lys
1               5                   10

<210> SEQ ID NO 12
<211> LENGTH: 14
<212> TYPE: PRT
<213> ORGANISM: Artificial sequence
<220> FEATURE:
<221> NAME/KEY: PEPTIDE
<222> LOCATION: 152..165
<223> OTHER INFORMATION: Mimecan cleavage peptide

<400> SEQUENCE: 12

Gly Asn Leu Ile Glu Asp Ile Glu Asp Gly Thr Phe Ser Lys
1               5                   10

<210> SEQ ID NO 13
<211> LENGTH: 6
<212> TYPE: PRT
```

```
<213> ORGANISM: Artificial sequence
<220> FEATURE:
<223> OTHER INFORMATION: N-terminal sequence of Mimecan peptide SEQ ID
      NO: 1

<400> SEQUENCE: 13

Asp Phe Ala Asp Ile Pro
1               5

<210> SEQ ID NO 14
<211> LENGTH: 6
<212> TYPE: PRT
<213> ORGANISM: Artificial sequence
<220> FEATURE:
<223> OTHER INFORMATION: N-terminal sequence of Mimecan peptide SEQ ID
      NO: 2

<400> SEQUENCE: 14

Thr Gly Asn Leu Ile Glu
1               5

<210> SEQ ID NO 15
<211> LENGTH: 6
<212> TYPE: PRT
<213> ORGANISM: Artificial sequence
<220> FEATURE:
<223> OTHER INFORMATION: N-terminal sequence of Mimecan peptide SEQ ID
      NO: 3

<400> SEQUENCE: 15

Leu Asp Phe Thr Gly Asn
1               5

<210> SEQ ID NO 16
<211> LENGTH: 6
<212> TYPE: PRT
<213> ORGANISM: Artificial sequence
<220> FEATURE:
<223> OTHER INFORMATION: N-terminal sequence of Mimecan peptide SEQ ID
      NOS: 5 and 6

<400> SEQUENCE: 16

Arg Leu Asp Phe Thr Gly
1               5

<210> SEQ ID NO 17
<211> LENGTH: 6
<212> TYPE: PRT
<213> ORGANISM: Artificial sequence
<220> FEATURE:
<221> NAME/KEY: PEPTIDE
<222> LOCATION: 271..276
<223> OTHER INFORMATION: N-terminal sequence of Mimecan peptide SEQ ID
      NO: 7

<400> SEQUENCE: 17

Arg Leu Glu Gly Asn Pro
1               5

<210> SEQ ID NO 18
<211> LENGTH: 6
<212> TYPE: PRT
<213> ORGANISM: Artificial sequence
<220> FEATURE:
<221> NAME/KEY: PEPTIDE
<222> LOCATION: 149..154
<223> OTHER INFORMATION: N-terminal sequence of Mimecan peptide SEQ ID
      NO: 8
```

```
<400> SEQUENCE: 18

Asp Phe Thr Gly Asn Leu
1               5

<210> SEQ ID NO 19
<211> LENGTH: 6
<212> TYPE: PRT
<213> ORGANISM: Artificial sequence
<220> FEATURE:
<221> NAME/KEY: PEPTIDE
<222> LOCATION: 221..226
<223> OTHER INFORMATION: N-terminal sequence of Mimecan peptide SEQ ID
      NO: 9

<400> SEQUENCE: 19

Asp His Asn Ala Leu Glu
1               5

<210> SEQ ID NO 20
<211> LENGTH: 6
<212> TYPE: PRT
<213> ORGANISM: Artificial sequence
<220> FEATURE:
<223> OTHER INFORMATION: N-terminal sequence of Mimecan peptide SEQ ID
      NO: 10

<400> SEQUENCE: 20

Asp Ile Asp Ala Val Pro
1               5

<210> SEQ ID NO 21
<211> LENGTH: 6
<212> TYPE: PRT
<213> ORGANISM: Artificial sequence
<220> FEATURE:
<223> OTHER INFORMATION: N-terminal sequence of Mimecan peptide SEQ ID
      NO: 11

<400> SEQUENCE: 21

Phe Thr Gly Asn Leu Ile
1               5

<210> SEQ ID NO 22
<211> LENGTH: 6
<212> TYPE: PRT
<213> ORGANISM: Artificial sequence
<220> FEATURE:
<223> OTHER INFORMATION: N-terminal sequence of Mimecan peptide SEQ ID
      NO: 12

<400> SEQUENCE: 22

Gly Asn Leu Ile Glu Asp
1               5

<210> SEQ ID NO 23
<211> LENGTH: 6
<212> TYPE: PRT
<213> ORGANISM: Artificial sequence
<220> FEATURE:
<223> OTHER INFORMATION: C-terminal sequence of Mimecan peptide SEQ ID
      NO: 1

<400> SEQUENCE: 23

Asp Ile Pro Asn Leu Arg
1               5

<210> SEQ ID NO 24
```

```
<211> LENGTH: 6
<212> TYPE: PRT
<213> ORGANISM: Artificial sequence
<220> FEATURE:
<223> OTHER INFORMATION: C-terminal sequence of Mimecan peptides SEQ ID
      NOS: 2, 3, 6, 8, and 11

<400> SEQUENCE: 24

Asp Gly Thr Phe Ser Lys
1               5

<210> SEQ ID NO 25
<211> LENGTH: 6
<212> TYPE: PRT
<213> ORGANISM: Artificial sequence
<220> FEATURE:
<223> OTHER INFORMATION: C-terminal sequence of Mimecan peptide SEQ ID
      NO: 4

<400> SEQUENCE: 25

Pro Ile Val Leu Gly Lys
1               5

<210> SEQ ID NO 26
<211> LENGTH: 6
<212> TYPE: PRT
<213> ORGANISM: Artificial sequence
<220> FEATURE:
<223> OTHER INFORMATION: C-terminal sequence of Mimecan peptide SEQ ID
      NO: 5

<400> SEQUENCE: 26

Asp Ile Glu Asp Gly Thr
1               5

<210> SEQ ID NO 27
<211> LENGTH: 13
<212> TYPE: PRT
<213> ORGANISM: Artificial sequence
<220> FEATURE:
<221> NAME/KEY: PEPTIDE
<223> OTHER INFORMATION: immunogenic peptide with linker at positions
      1 to 3

<400> SEQUENCE: 27

Gly Gly Cys Glu Asp Ile Glu Asp Gly Thr Phe Ser Lys
1               5                   10

<210> SEQ ID NO 28
<211> LENGTH: 10
<212> TYPE: PRT
<213> ORGANISM: Artificial sequence
<220> FEATURE:
<221> NAME/KEY: PEPTIDE
<222> LOCATION: 155..165
<223> OTHER INFORMATION: Mimecan peptide used as a screening peptide

<400> SEQUENCE: 28

Glu Asp Ile Glu Asp Gly Thr Phe Ser Lys
1               5                   10

<210> SEQ ID NO 29
<211> LENGTH: 11
<212> TYPE: PRT
<213> ORGANISM: Artificial sequence
<220> FEATURE:
<221> NAME/KEY: PEPTIDE
<223> OTHER INFORMATION: deselection peptide
```

```
<400> SEQUENCE: 29

Glu Asp Ile Glu Asp Gly Thr Phe Ser Lys Leu
1               5                   10

<210> SEQ ID NO 30
<211> LENGTH: 10
<212> TYPE: PRT
<213> ORGANISM: Artificial sequence
<220> FEATURE:
<221> NAME/KEY: PEPTIDE
<222> LOCATION: 151..160
<223> OTHER INFORMATION: Mimecan cleavage peptide

<400> SEQUENCE: 30

Thr Gly Asn Leu Ile Glu Asp Ile Glu Asp
1               5                   10
```